US010016154B2

(12) United States Patent
Shacham-Diamand et al.

(10) Patent No.: US 10,016,154 B2
(45) Date of Patent: Jul. 10, 2018

(54) PLACEABLE SENSOR AND METHOD OF USING SAME

(71) Applicant: Ramot at Tel-Aviv University Ltd., Tel-Aviv (IL)

(72) Inventors: Yosi Shacham-Diamand, Tel-Aviv (IL); Heftsi Ragones, Holon (IL); Amihay Freeman, Ramat-HaSharon (IL); David Schreiber, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 369 days.

(21) Appl. No.: 14/614,451

(22) Filed: Feb. 5, 2015

(65) Prior Publication Data
US 2015/0150493 A1 Jun. 4, 2015

Related U.S. Application Data

(63) Continuation-in-part of application No. PCT/IL2013/050666, filed on Aug. 5, 2013.
(Continued)

(51) Int. Cl.
*A61B 5/05* (2006.01)
*A61B 5/1473* (2006.01)
(Continued)

(52) U.S. Cl.
CPC .......... *A61B 5/1473* (2013.01); *A61B 1/3132* (2013.01); *A61B 5/1477* (2013.01);
(Continued)

(58) Field of Classification Search
USPC .............. 205/792; 204/403.01, 412; 29/825; 600/345
See application file for complete search history.

(56) References Cited

U.S. PATENT DOCUMENTS 4,478,222 A * 10/1984 Koning .............. A61B 5/14542
600/348
4,874,500 A 10/1989 Madou et al.
(Continued)

FOREIGN PATENT DOCUMENTS

| CN | 102735730 | 10/2012 |
| DE | 19842735 | 3/2000 |
| WO | WO 2014/024187 | 2/2014 |

OTHER PUBLICATIONS

International Preliminary Report on Patentability dated Feb. 19, 2015 From the International Bureau of WIPO Re. Application No. PCT/IL2013/050666.
(Continued)

*Primary Examiner* — Christian Jang
*Assistant Examiner* — Mitchell E Alter

(57) ABSTRACT

A sensor system is disclosed. The system comprises: a solid substrate having a front side and a back side, a sensing assembly formed on the front side and being configured to provide electrochemical sensing, a plurality of electrical contacts, formed on the back side and being in electrical communication with the sensing assembly via a plurality of interconnects passing through the substrate and extending at least from the front side to the back side, and a mounting member configured for mounting the back side onto a tip of a movable device.

17 Claims, 22 Drawing Sheets

Related U.S. Application Data

(60) Provisional application No. 61/679,740, filed on Aug. 5, 2012.

(51) Int. Cl.

| | | |
|---|---|---|
| *G01N 27/28* | (2006.01) | |
| *A61B 1/313* | (2006.01) | |
| *A61B 5/1477* | (2006.01) | |
| *A61B 17/34* | (2006.01) | |
| *G01N 27/327* | (2006.01) | |
| *A61B 5/00* | (2006.01) | |

(52) U.S. Cl.
CPC ....... *A61B 17/3423* (2013.01); *G01N 27/286* (2013.01); *G01N 27/327* (2013.01); *A61B 5/00* (2013.01); *Y10T 29/49117* (2015.01)

(56) References Cited

U.S. PATENT DOCUMENTS

| | | |
|---|---|---|
| 5,068,205 A | 11/1991 | Baxter et al. |
| 5,336,388 A | 8/1994 | Leader et al. |
| 5,497,772 A | 3/1996 | Schulman et al. |
| 5,660,163 A | 8/1997 | Schulman et al. |
| 6,022,463 A | 2/2000 | Leader et al. |
| 6,259,937 B1 | 7/2001 | Schulman et al. |
| 6,498,043 B1 | 12/2002 | Schulman et al. |
| 7,063,776 B2 | 6/2006 | Huang |
| 7,079,881 B2 | 7/2006 | Schulman et al. |
| 7,323,142 B2 | 1/2008 | Pendo et al. |
| 7,555,328 B2 | 6/2009 | Schulman et al. |
| 2002/0121439 A1 | 9/2002 | Crumley et al. |
| 2003/0049166 A1* | 3/2003 | Pendo .................. H05K 3/28 422/82.01 |
| 2003/0187338 A1* | 10/2003 | Say .................. A61B 5/14532 600/345 |
| 2006/0011474 A1 | 1/2006 | Schulein et al. |
| 2006/0219564 A1 | 10/2006 | Feng |
| 2007/0138027 A1* | 6/2007 | Dinsmoor .......... G01N 27/4035 205/787.5 |
| 2008/0247908 A1 | 10/2008 | Kahlman |
| 2008/0312524 A1 | 12/2008 | Solosko et al. |
| 2009/0301876 A1 | 12/2009 | Wagner et al. |
| 2010/0312063 A1* | 12/2010 | Hess .................. A61B 17/3423 600/204 |
| 2011/0036913 A1 | 2/2011 | Merz et al. |
| 2011/0124992 A1* | 5/2011 | Brauker ............. A61B 5/14532 600/345 |
| 2011/0203941 A1* | 8/2011 | Say .................. A61B 5/14532 205/775 |
| 2011/0213229 A1* | 9/2011 | Benoit ................ G01N 33/725 600/345 |
| 2012/0160679 A1 | 6/2012 | Suda et al. |
| 2013/0150689 A1* | 6/2013 | Shaw-Klein ........... G01N 27/30 600/345 |
| 2015/0219587 A1 | 8/2015 | Wang et al. |

OTHER PUBLICATIONS

International Search Report and the Written Opinion dated Nov. 25, 2013 From the International Searching Authority Re. Application No. PCT/IL2013/050666.

Toepper et al. "Biocompatible Hybrid Flip Chip Microsystem Integration for Next Generation Wireless Neural Interfaces", Proceedings of 56th Electronic Components and Technology Conference 2006, San Diego, CA, USA, p. 705-708, 2006.

Supplementary European Search Report and the European Search Opinion dated Feb. 2, 2016 From the European Patent Office Re. Application No. 13827917.9.

\* cited by examiner

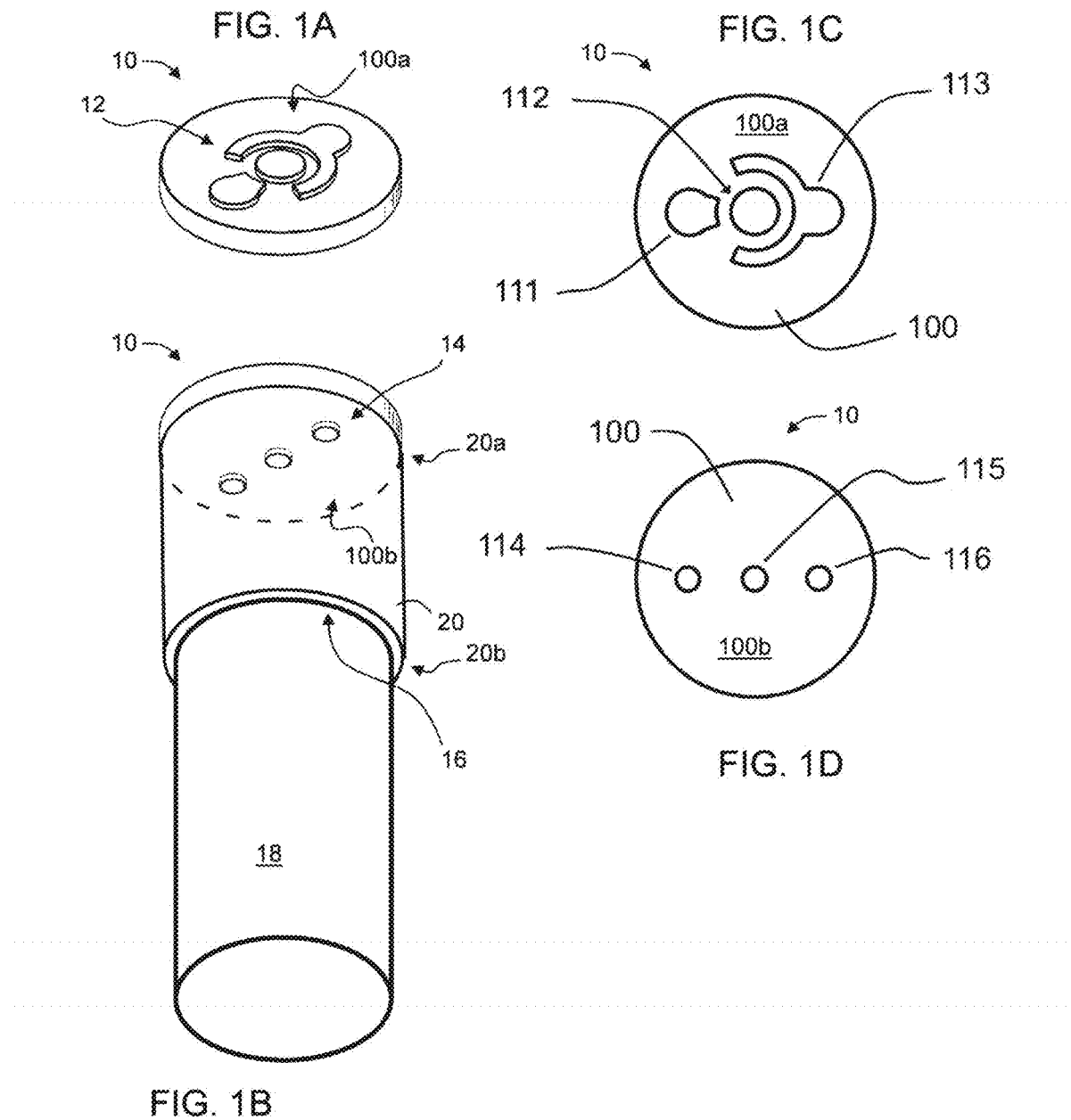

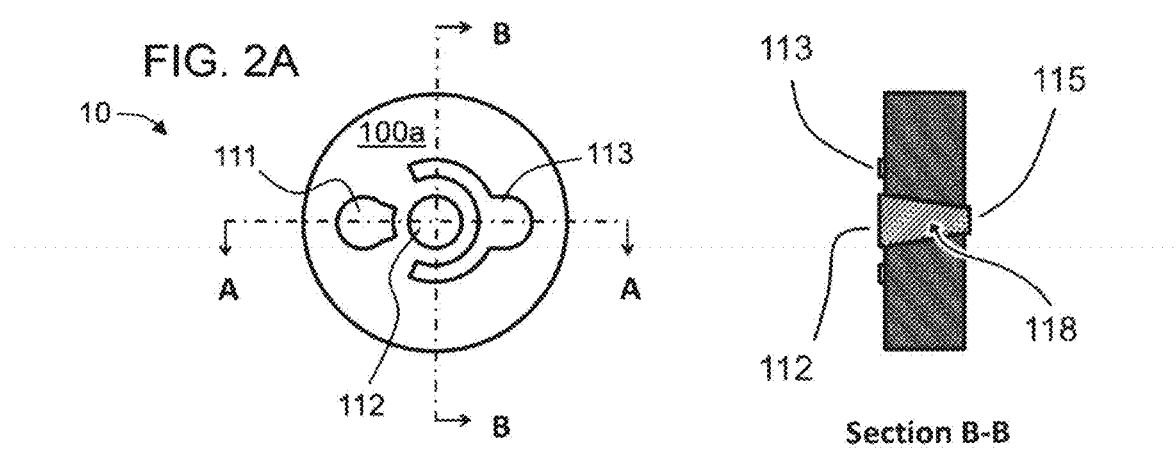
FIG. 2A
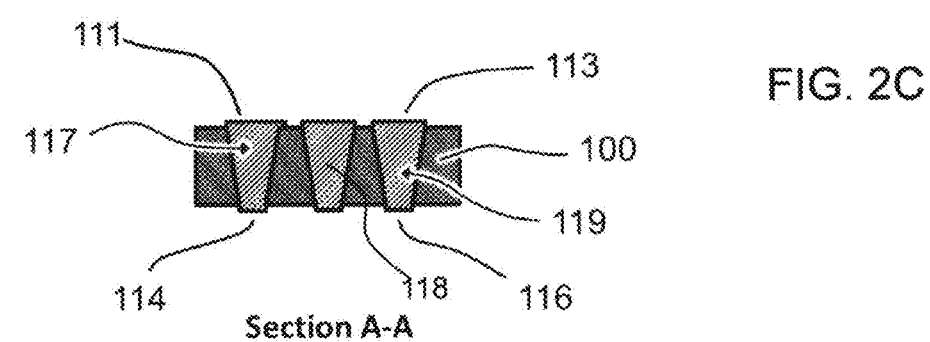
Section B-B
FIG. 2C
Section A-A
FIG. 2B

FIG. 3A
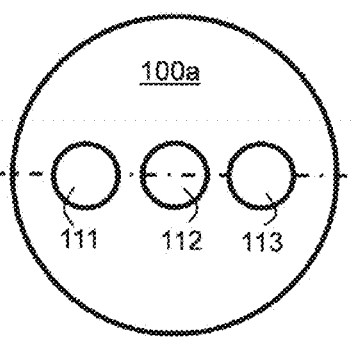
FIG. 3B
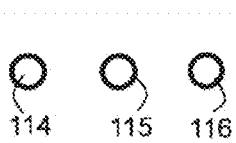
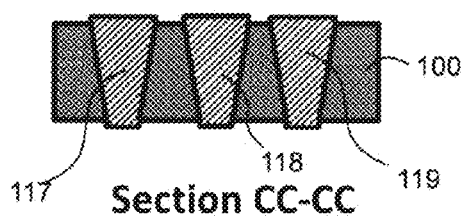
FIG. 3C

FIG. 4A
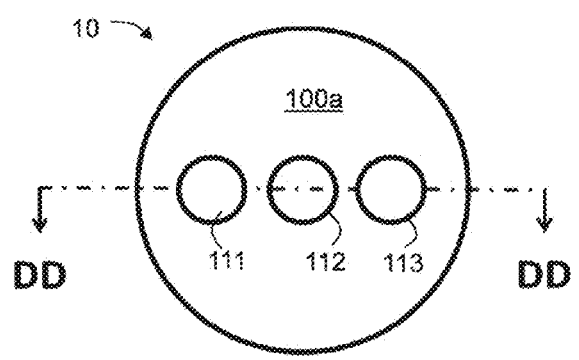
FIG. 4B
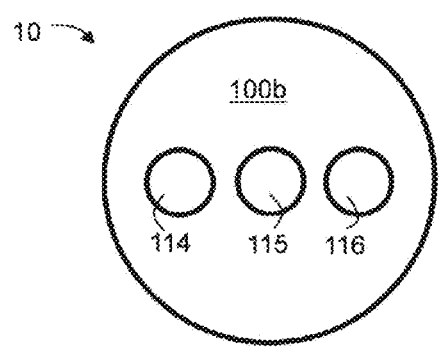
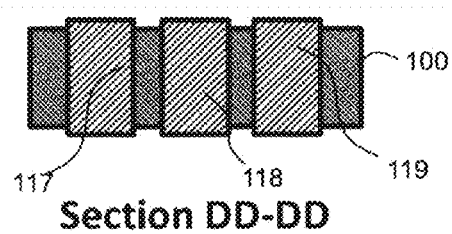
Section DD-DD
FIG. 4C

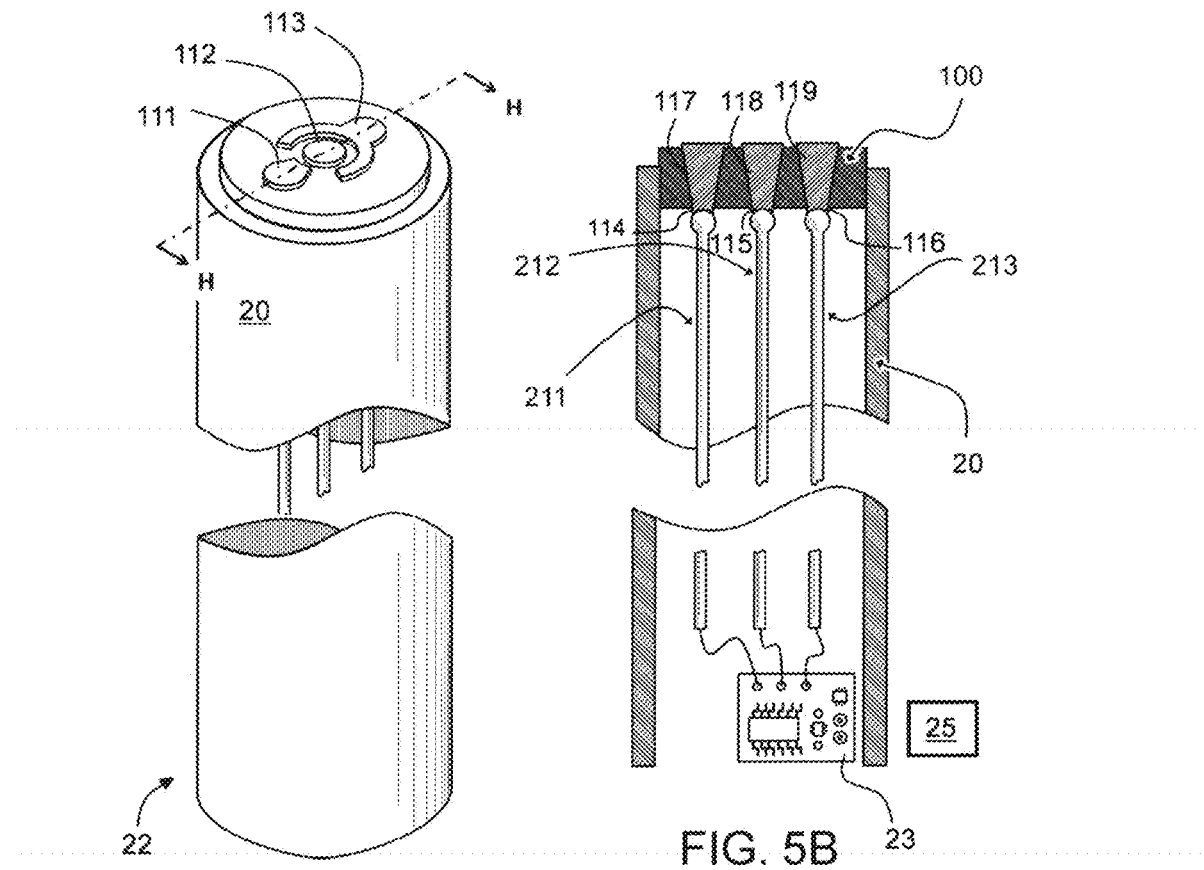
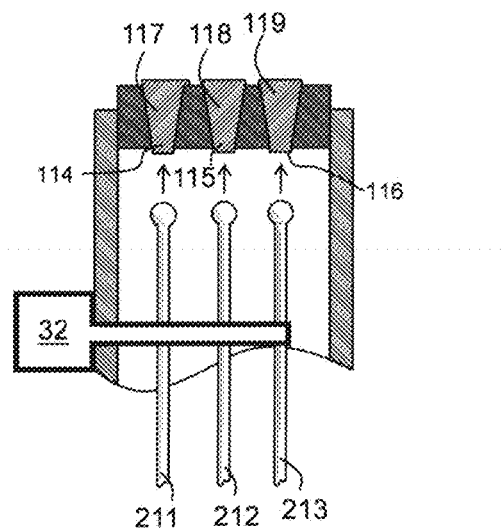
FIG. 5A
FIG. 5B
FIG. 5C

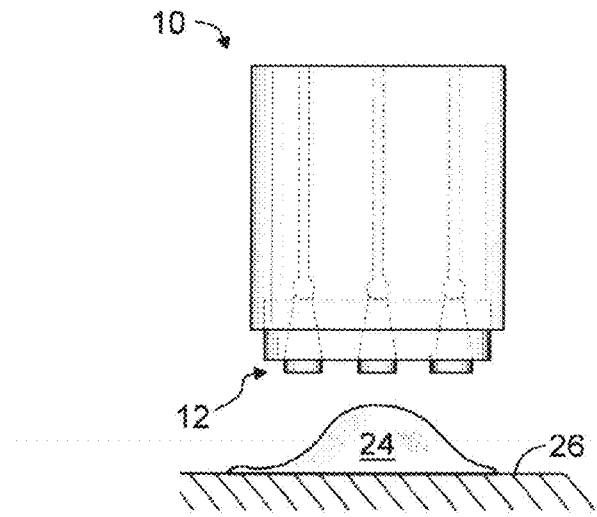
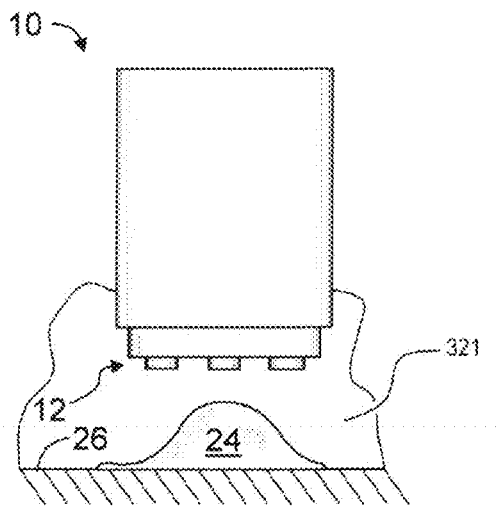
FIG. 6A          FIG. 6B
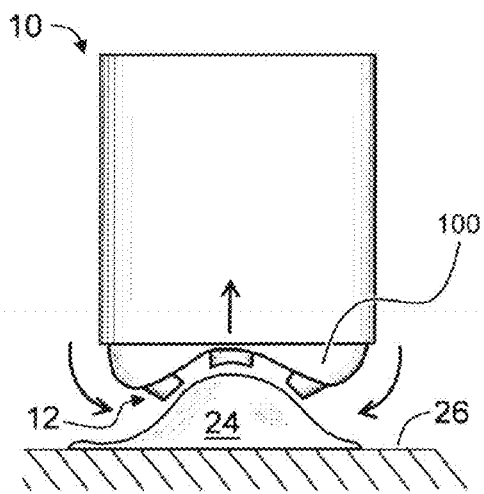
FIG. 6C

Section E-E

Section F-F

Section G-G

Section J-J

PLACEABLE SENSOR AND METHOD OF USING SAME

RELATED APPLICATIONS

This application is a Continuation-In-Part (CIP) of PCT Patent Application No. PCT/IL2013/050666 filed Aug. 5, 2013, which claims the benefit of priority of U.S. Provisional Patent Application No. 61/679,740 filed Aug. 5, 2012. The contents of the above applications are incorporated herein by reference in their entirety.

FIELD AND BACKGROUND OF THE INVENTION

The present invention, in some embodiments thereof, relates to a sensor and, more particularly, but not exclusively, to a sensor that is placeable on an organ or a sample, and to method of using such a sensor.

It is known to measure the concentration of a target substance to be analyzed in an aqueous liquid sample by placing the sample into a reaction zone of an electrochemical cell comprising two electrodes having an impedance which renders them suitable for amperometric measurement. The target substance is allowed to react directly or indirectly with a redox reagent whereby to form an oxidisable (or reducible) substance in an amount corresponding to the concentration of the target substance. The quantity of the oxidisable (or reducible) substance present is then estimated electrochemically.

Another approach involves the use of biosensors. Biosensors utilize molecular recognition capability of biomaterial, and use the biomaterial as a molecular recognizing element. When the biomaterial recognizes the target substance, it reacts and provides a signal. The biosensors utilize those reactions and measure the quantity of the target substance.

U.S. Pat. No. 6,022,463 discloses a sensor for use in a fluid analyte analyzer. The sensor includes a substrate, a subminiature through hole which traverses the substrate and which is filled with a conductive material, and a sensor electrode formed on a planar surface over the through hole. The conductive material disposed within the through hole is compatible with the material from which the sensor electrode is made.

U.S. Published Application No. 20080247908 discloses a microchip which includes a substrate, coupling circuits on a front side of the substrate, and electrical feed-through passages. The coupling circuits perform and process a wireless physical interaction. The feed-through passages connect a component of the coupling circuits to an externally accessible terminal which is disposed at a location remote from the front side of the substrate.

U.S. Published Application No. 20080312524 discloses a medical sensor which attaches to the body of a patient. The medical sensor includes an electrode layer having conductive material formed on a dielectric film. Electrodes and conductive traces are formed on the electrode layer from the conductive material. A motion sensor is formed from regions of conductive material that are formed on opposite sides of the dielectric film resulting in a capacitor structure. The conductive traces are configured with printed through-hole vias to provide electrical coupling from one side of the medical sensor to the other.

SUMMARY OF THE INVENTION

According to some embodiments of the invention the present invention there is provided a sensor system. The system comprises: a solid substrate having a front side and a back side; a sensing assembly formed on the front side and being configured to provide electrochemical sensing; a plurality of electrical contacts, formed on the back side and being in electrical communication with the sensing assembly via a plurality of interconnects passing through the substrate and extending at least from the front side to the back side; and a mounting member configured for mounting the back side onto a tip of a movable device.

According to some embodiments of the invention the movable device is a hand-held device.

According to some embodiments of the invention the movable device is a movable arm of a robot.

According to some embodiments of the invention the movable device is an internal medical tool selected from the group consisting of an endoscope, a laparoscope and a cannula, and wherein the substrate is adapted for being introduced into the body of a mammal via endoscopic procedure.

According to some embodiments of the invention the movable device is an external medical tool.

According to some embodiments of the invention the substrate is sizewise comparable with the tip.

According to some embodiments of the invention the electrochemical sensing assembly comprises at least a working electrode, a reference electrode and a counter electrode.

According to some embodiments of the invention the front side is non-adhesive to tissue.

According to some embodiments of the invention the interconnects have a shape selected from the group consisting of a generally conical shape, a generally cylindrical shape, and an hourglass shape.

According to some embodiments of the invention the substrate is flexible.

According to some embodiments of the invention the system comprises further comprising the movable device.

According to some embodiments of the invention the mounting member comprises an adhesive.

According to some embodiments of the invention the mounting member comprises a housing configured to receive the substrate at a front side of the housing and the hand-held device at a back side of the housing.

According to an aspect of some embodiments of the present invention there is provided a method which comprises providing a movable device and mounting the sensor system described above, on the movable device using the mounting member.

According to an aspect of some embodiments of the present invention there is provided a method of sensing a target substance. The method comprises contacting the target substance with the sensor system as described above and receiving signals from the plurality of electrical contacts, thereby sensing the target substance.

According to an aspect of some embodiments of the present invention there is provided a method of sensing a target substance. The method comprises maintaining a surface substantially at rest, placing a sensing assembly on the surface, and operating the sensing assembly for determining presence, absence or level of the target substance on the surface; wherein the sensing assembly is formed on a front side of a solid substrate and being configured to provide electrochemical sensing; and wherein the operating the sensing assembly comprises receiving electrical signals from a plurality of electrical contacts formed on a back side of the substrate and being in electrical communication with the sensing assembly via a plurality of interconnects passing through the substrate and extending at least from the front side to the back side.

According to some embodiments of the invention the placement of the sensing assembly on the surface, comprising approaching the surface from above.

According to some embodiments of the invention the placement of the sensing assembly on the surface, comprising approaching the surface from the side.

According to some embodiments of the invention the surface is a skin surface of a living body.

According to some embodiments of the invention the surface is a surface of an internal organ of a living body, and wherein the placing is executed endoscopically or laparoscopically.

According to some embodiments of the invention the placement is executed in vitro.

According to some embodiments of the invention the surface is a surface of a sample in a well of a multi-well plate, and the sensing assembly is placed in the well from above.

According to an aspect of some embodiments of the present invention there is provided a sensor system. The system comprises: a movable device having a handle and a tip; a solid substrate, mounted on the tip and having a front side and a back side; a sensing assembly formed on the front side and being configured to provide electrochemical, electrobiochemical, pressure or electrical sensing; and at least one electrical contact, formed on the back side and being in electrical communication with the sensing assembly via at least one interconnect passing through the substrate and extending at least from the front side to the back side.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D are schematic illustrations of a sensor system, according to some embodiments of the present invention;

FIGS. 2A-C are schematic illustrations of the sensor system in embodiments of the invention in which the electrodes are patterned and the interconnects are generally conical;

FIGS. 3A-C are schematic illustrations of the sensor system in embodiments of the invention in which the electrodes are circular and the interconnects are generally conical;

FIGS. 4A-C are schematic illustrations of the sensor system in embodiments of the invention in which the electrodes are circular and the interconnects are generally cylindrical;

FIGS. 5A-C are schematic illustrations of the sensor system in embodiments of the invention in which the system comprises a plurality of electrical leads for connecting the electrical contacts to a measuring device;

FIGS. 6A-C are schematic illustrations showing procedures for sensing a target substance on a surface, in embodiments of the invention in which the surface is approached from above;

DESCRIPTION OF SPECIFIC EMBODIMENTS OF THE INVENTION

Figure 7A:
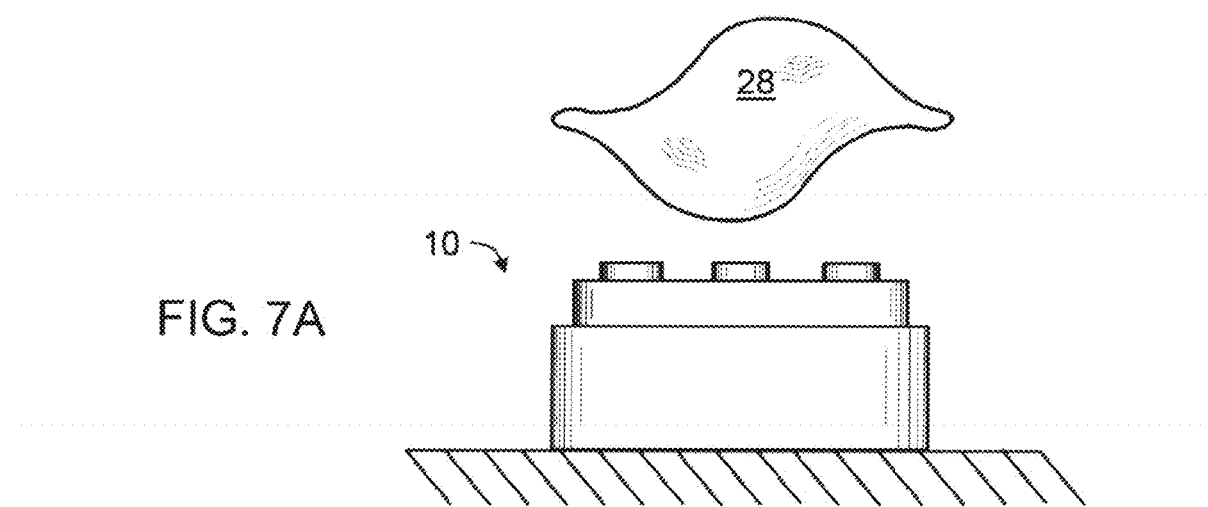
FIGS. 7A-D are schematic illustrations showing procedures for sensing a target substance, in embodiments of the invention in which the target substance is above the sensor system.

The present invention, in some embodiments thereof, relates to a sensor and, more particularly, but not exclusively, to a sensor that is placeable on an organ or a sample, and to method of fabricating and using such a sensor.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIGS. 1A-D illustrate a sensor system 10, according to some embodiments of the present invention. System 10 comprises a solid substrate 100 having a front side, generally shown at 100a (FIGS. 1A and 1C) and a back side generally shown at 100b (FIGS. 1B and 1D).

In various exemplary embodiments of the invention front side 100a is made non-adhesive to tissue, optionally and preferably to skin-tissue.

The term "non-adhesive to tissue," as used herein, refers to a surface of a substrate which is detachable from a tissue being in contact with the surface, wherein gravitational forces resulting only from the weight of the substrate are sufficient to effect the detachment.

In some embodiments of the present invention cells and/or cell processes do not adhere to front side 100a is at the molecular level.

Substrate 100 is optionally and preferably sizewise comparable with a tip 16 of a movable device 18, such as, but not limited to, a hand-held device or a movable arm of a robot. Device 18 can be, for example, an internal medical tool constituted for intracorporeal use, e.g., an endoscope, a laparoscope, a cannula, or an external medical tool constituted for extracorporeal use, e.g., a medical pen, a medical shaft or the like. In some embodiments of the present invention the largest dimension of substrate 100 is at most 2 mm or at most 1.5 mm or at most 1 mm or less.

Suitable materials for substrate 100 include, without limitation, a polymer, for example, an elastomeric polymer such as, but not limited to, polydimethylsiloxane (PDMS) and polytetrafluoroethylene (PTFE), silicone or the like.

System 10 further comprises a sensing assembly 12 formed on front side 100a. In various exemplary embodiments of the invention sensing assembly 12 is configured to provide electrochemical sensing.

As used herein, "electrochemical sensing" refers to a process in which a sensible electrical signal is generated responsively to chemical reaction.

As used herein, "chemical reaction" refers to a reaction wherein one or more new species are produced by the chemical change of one or more components when certain conditions are provided for them to react.

The present embodiments contemplate electrochemical sensing which is effected by a process in which a sensible electrical signal is generated responsively to biochemical reaction. Such sensing is encompassed by the term electrochemical sensing and is referred to below as electrobiochemical sensing.

As used herein "biochemical reaction" refers to a reaction between two or more substances, wherein at least one of the substances is a biological material.

As used herein "biological material" refers to any material derived or obtained from a biological source, wherein the biological source has at least the complexity of a cell. In some embodiments of the present invention "biological material" refers to a material derived or obtained from a living organism.

According to some embodiments of the present invention electrobiochemical sensing is a process in which sensible electrical signal is generated responsively to biochemical reaction, wherein the biochemical reaction is a reaction that employs at least one of biological material selected from the group consisting of the product(s) of an amplification reaction, including both target and signal amplification, a purified sample, such as purified genomic DNA, RNA, protein, etc, a raw samples (bacteria, virus, genomic DNA, etc.), a biological molecular compound such as, but not limited to, a nucleic acid and related compounds (e.g., DNA, RNA, oligonucleotide or analogs thereof, PCR product, genomic DNA, bacterial artificial chromosome, plasmid and the like), a protein and related compounds (e.g. a polypeptide, a peptides, a monoclonal or polyclonal antibody, a soluble or bound receptor, a transcription factor, and the like), an antigen, a ligand, a hapten, a carbohydrate and related compounds (e.g. polysaccharide, a oligosaccharides and the like), a cellular fragment such as a membrane fragment, a cellular organelle, an intact cell, a bacteria, a virus, a protozoa, and the like.

In some embodiments of the present invention sensing assembly is configured for electrochemical sensing which all the reactants that participates in the chemical reaction are non-biological.

In some embodiments of the present invention sensing assembly is configured for pressure sensing, and in some embodiments of the present invention sensing assembly is configured for electrical sensing.

Pressure sensing can be used, for example, for measuring the rigidity of a target material. In embodiments of the invention in which sensing assembly 12 is configured for pressure sensing, substrate 100 is optionally and preferably made flexible, such that when assembly 12 is brought into contact with the substance it experiences a strain which depends on the rigidity of the target material. The strain can be detected, for example, as a change of electrical resistance, voltage or capacitance of sensor system 10.

Electrical sensing can be used for measuring the potential of the target material. In these embodiments, when sensor system 10 is brought into contact with the substance a voltage potential can be generated and monitored. For example, healthy tissue and non-healthy tissue generate quantifiably different potentials which can then be output by the sensing system of the present embodiments.

Sensing assembly 12 comprises a plurality of electrodes. In the representative example shown in FIGS. 1A and 1C, assembly 12 comprises three electrodes designated by reference numerals 111, 112 and 113. For example, electrode 112 can be a working electrode, electrode 113 can be a counter electrode, and electrode 111 can be a reference electrode. The working electrode is the electrode at which the electrochemical or biochemical reaction occurs. Depending on the type of reaction, the working electrode can serve as a cathode or as an anode. Suitable materials for the working electrode including, without limitation, carbon (e.g., glassy carbon, activated carbon cloth, carbon felt, platinized carbon cloth, plain carbon cloth), gold, platinum, silver and the like. The counter electrode is optionally and preferably, but not necessarily, made of the same material as the working electrode. The reference electrode can be a Silver/Silver Chloride electrode, a calomel (e.g., saturated calomel) electrode, or the like.

Electrodes 111, 112 and 113 are illustrated as patterned electrodes, wherein electrode 111 is shaped generally as a horseshoe, electrode 112 is generally circular and electrode 113 has the shape of a truncated oval. However, this need not necessarily be the case, since, for some applications, it may not be necessary for the electrode to have those specific shapes or to be patterned. A representative example of a configuration with three circular electrodes is illustrated in FIGS. 3A-C. Further, although FIGS. 1A-D show a three electrode configuration, it is not intended to limit the scope of the present invention to a configuration with three electrodes.

In embodiments in which sensing assembly 12 provides electrobiochemical sensing, the biological material is preferably immobilized at the front side 100a of substrate 100, near or on one of the electrodes.

In various exemplary embodiments of the invention sensor system comprises a plurality of electrical contacts 14 formed on back side 100b of substrate 100. Contacts 14 are in electrical communication with sensing assembly 12 via a plurality of interconnects passing through substrate 100 and extending from front side 100a to backside 100b. The number of electrical contacts on back side 100b is preferably the same as the number of electrodes in assembly 12, such that each contact is in electrical communication with one electrode of assembly 12, and is preferably devoid of any electrical communication with the other electrodes of assembly 12. FIGS. 1B and 1D are schematic illustrations of an embodiment in which back side 100b comprises three electrical contacts. In FIG. 1D, the three contacts are designated 114, 115 and 116. For example, contact 114 can be in electrical communication with electrode 111, contact 115 can be in electrical communication with electrode 112, and contact 116 can be in electrical communication with electrode 113.

The interconnects of system 10 are illustrated in FIGS. 2A-C, where FIG. 2A shows front side 100a, FIG. 2B is a cross-sectional view of substrate 100 along the line A-A in FIG. 2A, and FIG. 2C is a cross-sectional view of substrate 100 along the line B-B in FIG. 2A. FIGS. 2A-C correspond to a three-electrode configuration. In this configuration, system 10 preferably comprises three interconnects shown at 117, 118 and 119. FIGS. 2B and 2C illustrate interconnects having a generally conical shape. Other interconnect shapes, including, without limitation, generally cylindrical shape and hourglass shapes, are not excluded from the scope of the present invention.

A representative example of a three-electrode configuration in which the electrodes are circular and the interconnects are generally cylindrical are illustrated in FIGS. 4A-C.

System 10 optionally and preferably comprises a mounting member 20 configured for mounting back side 100b onto a movable device 18. Mounting member 20 is shown in FIG. 1B as a housing which receives substrate 100 at a front side 20a of the housing and device 18 at the back side 20b of the housing. Other types of mounting members are not excluded from the scope of the present invention. For example, mounting member can comprise an adhesive selected top adhere back side 100b on device 18.

Before providing a further detailed description of the sensor system of the present embodiments, attention will be given to the advantages and potential applications offered thereby.

Sensor system 10 optionally and preferably allows monitoring secreted analytes by approaching from their upper surface. Conventional integrated electrodes, particularly those that provide electrochemical sensing, include electrodes and electrical contacts patterned on the top surface of a substrate. This configuration requires the integration of cells with the electrode's surface and the measurement of analytes secreted into the contact region. This process requires a preliminary step of detachment of the cells to be tested from their origin, and results in poor signal-to-noise ratio. Signal strength and device sensitivity can be increased by minimizing the gap between the cells and the sensor.

The present embodiments overcome at least a few of these limitations. The sensor system of the present embodiments comprises sensing electrodes on a substrate which can be placed on an exposed surface of a sample, wherein the signals are output from the opposite side of the substrate (not in contact with the sample). Thus signals flow along a path perpendicular to the substrate and sample being measured. Electrical communication between the electrodes on one side of the substrate and electrical contacts at the opposite side of the substrate can be established by interconnects, interchangeably referred to herein as vias.

The approach of the present embodiments paves the way to perform direct, non-invasive diagnostics of an exposed cell layer both for in-vivo and in-vitro applications. The system of the present embodiments is useful for many medical and health care applications.

Thus, in use, sensor system 10 can be mounted on a hand-held device using the mounting member 20. A target substance, such as, but not limited to, a cell can be contacted with the sensing assembly and electrical signals can be received from the electrical contacts 114, 115 and 116. The signals can be measured by any technique known in the art including, without limitation, chrono-amperometry, chrono-potentiometry, cyclic voltammetry, chrono-coulometry and square wave voltammetry.

FIGS. 5A-C are schematic illustrations of system 10 in embodiments of the invention in which system 10 comprises a plurality of electrical leads 211, 212 and 213 for connecting electrical contacts 114, 115 and 116 to a measuring device 22. The electrical leads are made of a conductive material such as a metal, and can be made flexible or rigid as desired. In embodiments in which system 10 comprises housing 20, the leads optionally and preferably occupy the interior of housing 20, as illustrated in FIGS. 5A-C.

Measuring device 22 typically comprises an electronic circuit 23 configured for receiving and measuring the electrical signal from the electrical contacts. Measuring device 22 can be encapsulated within housing 20 or it can be external to housing 20.

The measuring device optionally and preferably communicates with a data processor 25 supplemented by software for receiving, analyzing and presenting data pertaining to the measurement.

As used herein, "data processor" includes any suitable device for processing data, including, without limitation, a microcomputer, a microprocessor, and a data processing system. A data processor can be electronic computing circuitry (e.g., a central processing unit) or a system associated with such circuitry. Representative examples include, without limitation, a desktop home computer, a workstation, a laptop computer and a notebook computer. Also contemplated is a dedicated system having electronic computing circuitry therein. Optionally, such a dedicated system is portable. Optionally, such a dedicated system is hand held or wearable, e.g., on the arm of the user. Also contemplated are systems which are capable of receiving and processing data but may also have other functions. Representative examples include, without limitation, a cellular telephone with data processing functionality (also known as a smartphone), a personal digital assistant (PDA) with data processing functionality, a portable email device with data processing functionality (e.g., a BlackBerry® device), a portable media player with data processing functionality (e.g., an Apple iPod®), a portable gaming device with data processing functionality (e.g., a Gameboy®), and a tablet or touch screen display device with data processing functionality (e.g., an Apple iPad®, the Motorola Xoom®, Samsung Galaxy®, and the TabletKiosk Sahara NetSlate®).

The communication between data processor 25 and measuring device 22 is optionally and preferably by an electronic signal is transmitted through an interface such as, but not limited to, an IEEE 1394 interface, a USB interface, a wireless interface and the like. Wireless interface may feature, for example, Bluetooth communication, IEEE 802.11(b) (WiFi) communication, Wi-Max communication, or wireless USB communication.

Data processor 25 is preferably supplemented by software programmed for receiving electrical signals from measuring device 22, analyzing the signal and presenting an output pertaining to the analysis. The software is optionally and preferably also designed for providing a virtual user interface, e.g., by means of a tough or multi-touch screen, so as to allow the user to interact with the data processor.

In some embodiments of the present invention the leads are not in contact with the electrical contacts. Prior to sensing, leads can be engaged to make contact with the electrical contacts. The engagement can be realized by an engaging mechanism 32 configured to push the leads toward the electrical contacts (FIG. 5C). Mechanism 32 can be of the type typically used in, for example, a retractable ballpoint pen.

FIGS. 6A-C are schematic illustrations showing procedures for sensing a target substance 24 on a surface 26. Existence, absence or level of target substance 24 on surface 26 can be sensed, according to some embodiments of the present invention, by placing sensing assembly 12 of sensor system 10 on the surface while maintaining the surface substantially at rest. For example, sensor system 10 can approach the surface from above or from the side or from below. In the embodiments illustrated in FIGS. 6A-C, system 10 approaches surface 26 from above. As shown, sensor system 10 is placed on top of surface 26 such that surface 26 is below sensor system 10.

Surface 26 can be, for example, a skin surface of a living body, in which case sensor system 10 is preferably mounted on an external medical tool constituted for extracorporeal use, e.g., a medical pen, a medical shaft or the like. The surface can alternatively be an internal organ of a living body, in which case sensor system 10 is preferably mounted on an endoscope or a laparoscope, and the placement is executed endoscopically or laparoscopically. Still alternatively, the placement can be executed in vitro.

The sensing of substance 24 can be in the presence of a fluid or gel medium 321 as illustrated in FIG. 6B. Representative examples of fluid media including, without limitation, saliva, blood, urine and buffer solution. Representative examples of gel media including, without limitation, conductive gel, e.g., ultrasound gel, polyacrylamide. In these embodiments, medium 321 is optionally and preferably applied to surface 26 before approaching the surface with system 10. Alternatively the gel medium can be dispensed by, or through, sensor system 10. In some embodiments of the present invention substrate 100 is made flexible. These embodiments are advantageous since the flexibility of substrate 100 allows sensing assembly to conform with the shape, or to measure the mechanical stiffness, of substance 24 and/or surface 26, as illustrated in FIG. 6C.

Figure 7B:
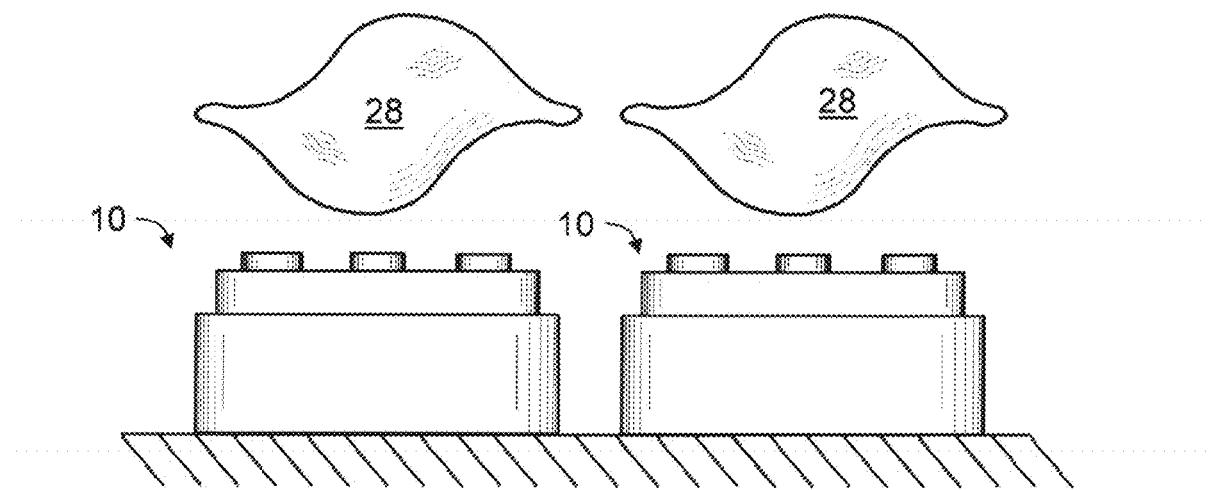
Figure 7C:
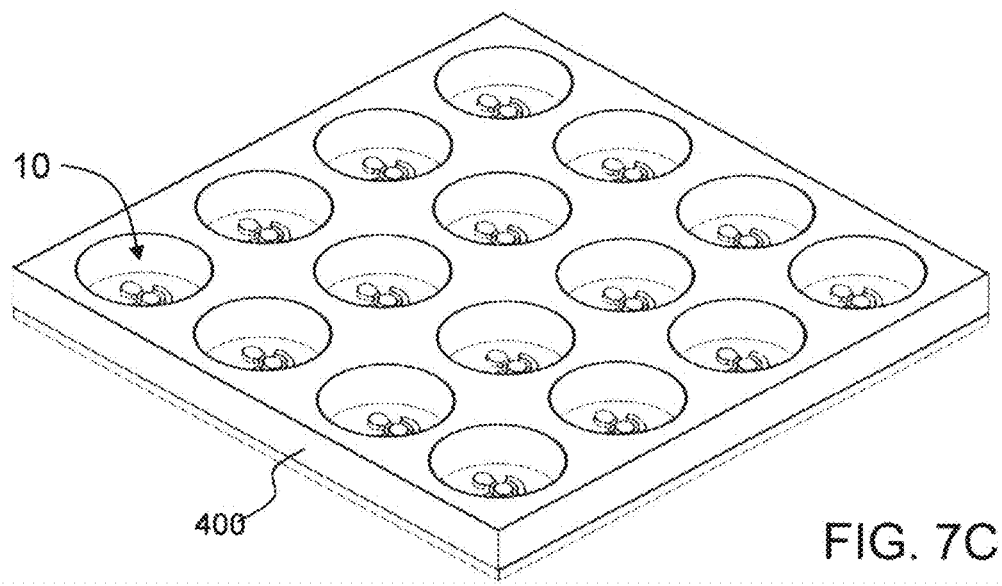
Figure 7D:
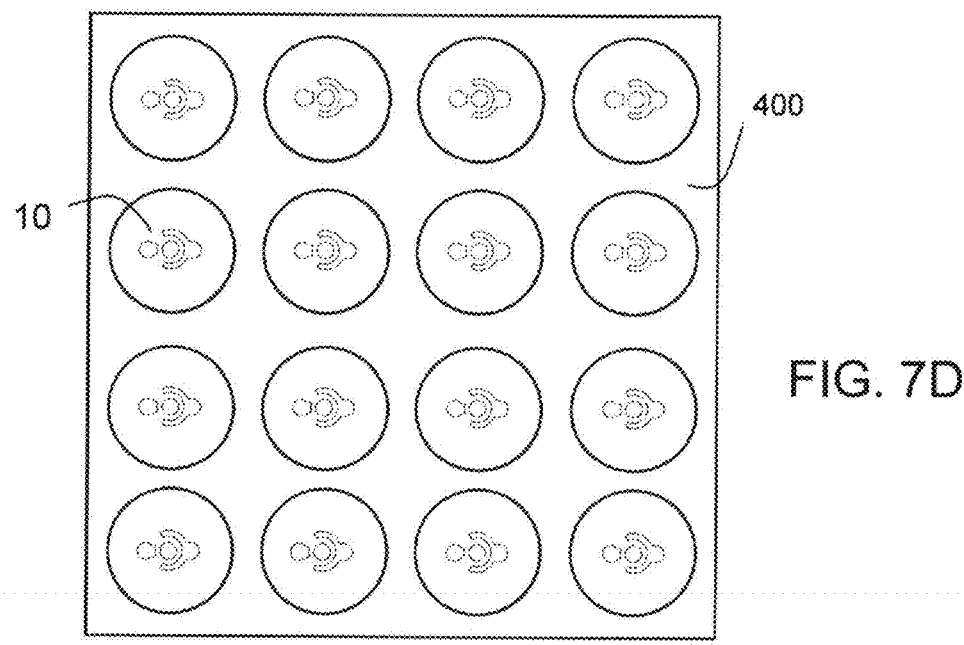

While FIGS. 6A-C illustrate embodiments in which sensor system 10 is above substance 24, it is to be understood other positional relations between system 10 and substance 24 are not excluded from the scope of the present invention. FIGS. 7A-D illustrate embodiment of the invention in which the target substance is above system 10. FIG. 7A illustrates an embodiment in which a sample 28 (e.g., a tissue sample or a cell) to be analyzed is placed on sensor system 10. FIG. 7B illustrates an embodiment in which two or more sensor systems, each being similar or the same as sensor system 10, operate together. As shown, a sample to be analyzed is placed on each of the systems. FIGS. 7C-D illustrate an embodiment of the invention in which a plurality of sensor systems, each being similar or the same as sensor system 10, is integrated in a respective plurality of wells arranged as an array 400. For example, the wells can be wells of a microwell plate wherein the sensor system of the present embodiments is integrated on the base of each well.

Figure 8A:
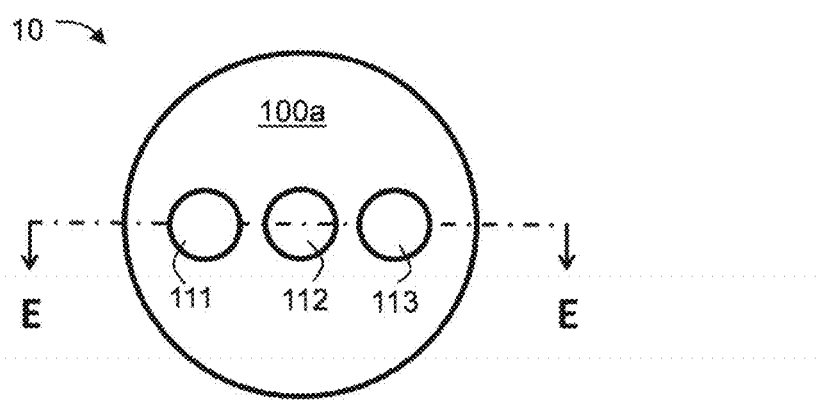
FIGS. 8A-B are schematic illustrations of the sensor system in exemplary embodiments of the invention in which one or more of electrodes is coated.
Figure 8B:
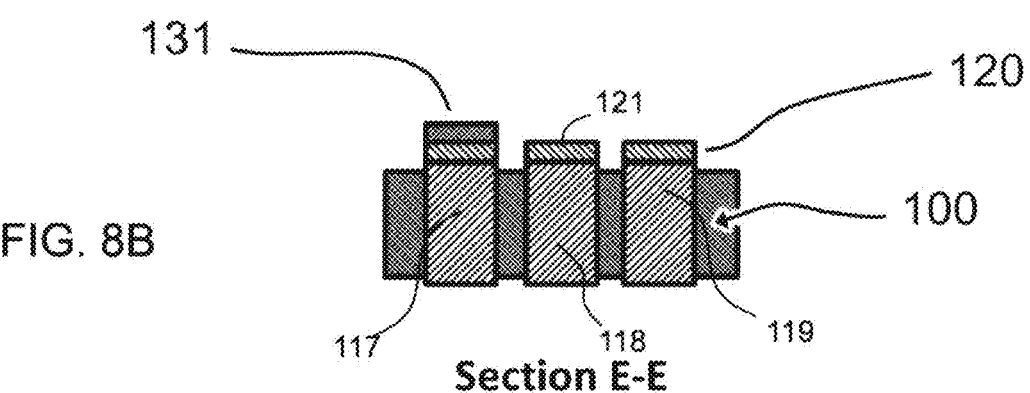

FIGS. 8A-B are schematic illustrations of system 10 in exemplary embodiments of the invention in which one or more of electrodes 111, 112 and 113 is coated.

In some embodiments of the present invention electrodes 111, 112 and 113 are coated by metal layers 120, 121 and 122, respectively, and the reference electrode (electrode 111 in the present example) is further coated by a layer 131 of a reference material. Suitable materials for use as a metal layer include, without limitation, carbon (e.g., glassy carbon, activated carbon cloth, carbon felt, platinized carbon cloth, plain carbon cloth), gold, platinum, silver and the like. Suitable reference materials include, without limitation, Silver/Silver Chloride electrode, a calomel (e.g., saturated calomel) electrode, or the like. A typical thickness for layers 120, 121 and 122 is from about 100 nm to about 7 μm. A typical thickness for layer 131 is from about 100 nm to about 7 μm.

Sensor system 10 of the present embodiments can be fabricated in more than one way.

Figure 11A:
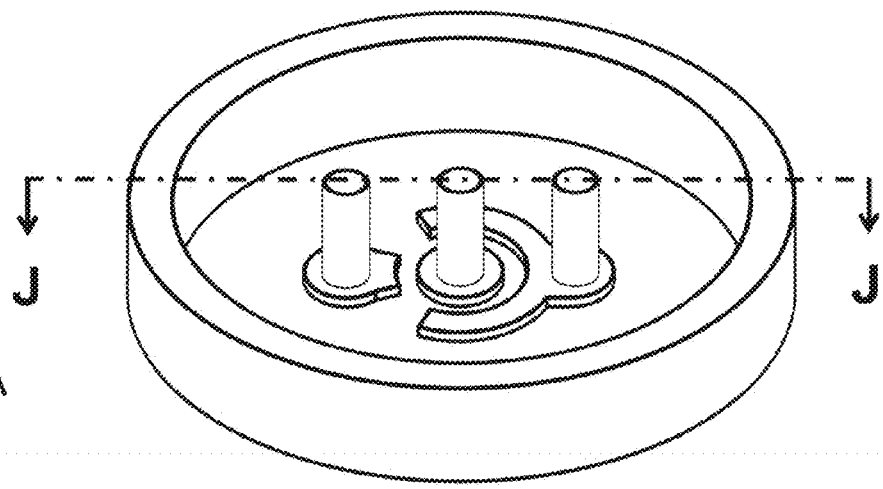
FIGS. 11A-E are schematic illustrations of a process suitable for fabricating a sensor system, according to some embodiments of the present invention.
Figure 11B:
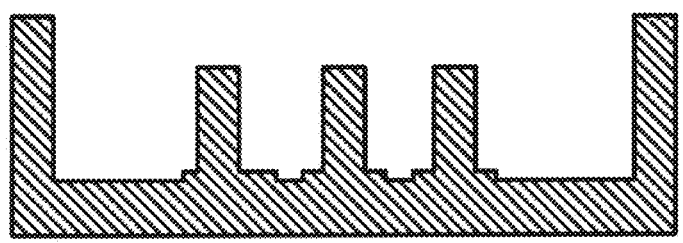
Figure 11C:
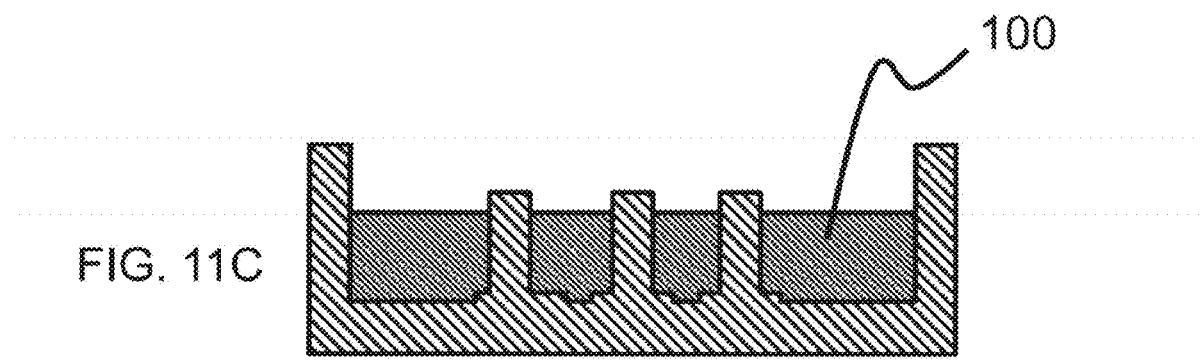
Figure 11D:
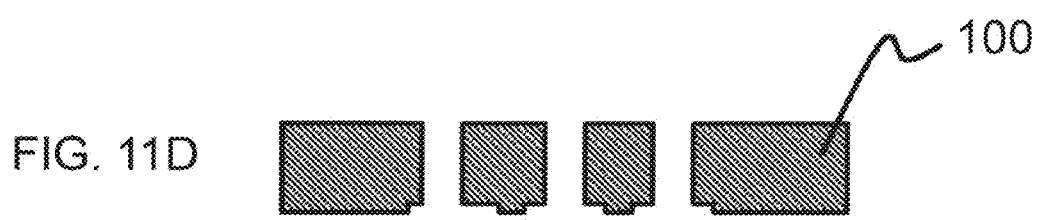

In some embodiments of the present invention a mold is fabricated, for example, using a three-dimensional fabrication process (e.g., stereolithography, 3D printing) and the like. A representative example of a mold 140 suitable for use according to some embodiments of the present invention is illustrated in FIGS. 11A (perspective view) and 11B (cross sectional view). The mold preferably includes shaped protrusions 142 at the locations of the interconnects. The shapes of protrusions 142 is the same as the shape of the interconnects to be formed (e.g., cylindrical, conical, hourglass), as further detailed hereinabove. Optionally and preferably, the mold also comprises a relief pattern 144 at the bases of protrusions 142, wherein the shape of pattern 144 is the same as the shape of the electrodes to be formed as further detailed hereinabove. A polymeric material, such as, but not limited to, PDMS can then be introduced into the mold and cured thereafter to form a patterned substrate, with vias at the locations of protrusions 142 and with grooves at the locations of pattern 144. FIG. 11C is a cross sectional view of mold 140, following the introduction of a polymeric material 146 into the mold. Following curing, the patterned substrate can be separated from the mold. FIG. 11D illustrates the patterned substrate 100, including the vias (generally shown at 148) and the grooves (generally shown at 150), following the separation between the substrate and the mold.

Figure 11E:
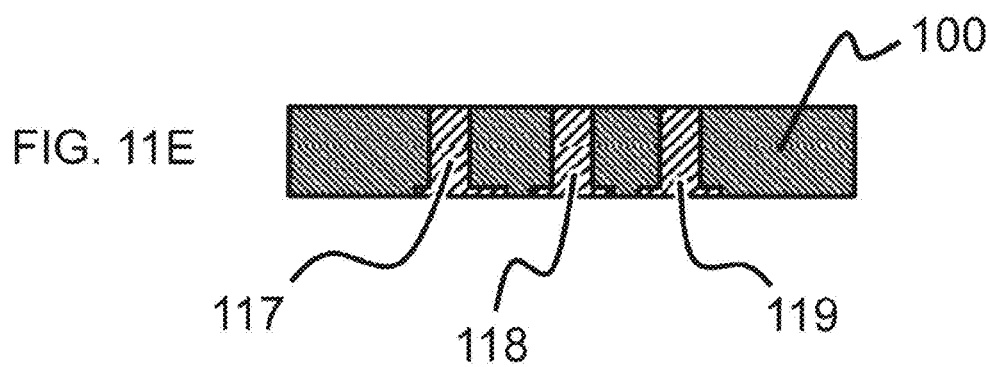

A conductive composition can be patterned on the substrate, to fill the vias and grooves, as illustrated in FIG. 11E. A metallization process can then be employed to form the electrodes and electrical contacts. A stencil or shadow mask defining the electrodes can then fabricated, for example, from a polyimide film, metal, plastic and glass. Any metallization process can be employed, including, without limitation, sputter deposition, evaporation and electroplating. Preferably, a reference electrode is also fabricated as known in the art. In a representative embodiment, a metal plating is followed by chloridation and anodization.

The conductive composition optionally and preferably comprises a polymer and an electrically conductive additive. The weight or volume ratio between the polymer and the additive can be selected based on the desired conductivity and mechanical characteristics of the conductive composition, as known in the art. In some embodiments of the present invention a conductive PDMS, which include a mixture of PDMS and an electrically conductive additive, is used. In experiments performed by the present inventors a conductive PDMS was form by mixing PDMS with graphite. Other electrically conductive additives suitable for the present embodiments include, without limitation, ethylenedioxythiophene (EDOT), poly(3,4-ethylenedioxythiophene) (PEDOT), PEDOT doped with poly(styrenesulfonate), polyaniline, poly(pyrrole), poly(acetylene), poly(thiophene), poly(p-phenylene sulfide), poly(para-phenylene vinylene), polyindole, polypyrene, polycarbazole, polyazulene, polyazepine and polynaphthalene.

An alternative fabrication process suitable for some embodiments of the present invention includes deposition of metal, e.g., gold on the front side of a silicon wafer. The other side can be patterned with lithographic techniques to define the interconnects. Vias can be etched using any suitable etching process, such as, but not limited to, wet chemical etching, dry chemical etching and physical etching. The etching is preferably termination when the metal layer on the front side is reached. The vias can alternatively formed by drilling, e.g., by laser ablation. The thus formed vias can then be filled with conductive material, e.g., a metal, such as, but not limited to, gold. This can be done, for example, by electroplating technique. The metal layer on the front side can then be patterned, e.g., by lithography, and etched to define the electrodes. Preferably, a reference electrode is also fabricated as known in the art.

Figure 9A:
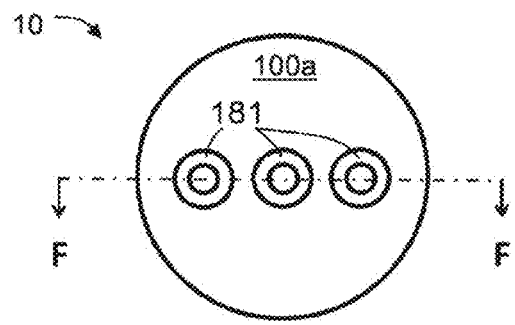
FIGS. 9A-B are schematic illustrations of shadow masks applied at the front side of a substrate and vias are filled with conductive material.
Figure 9B:
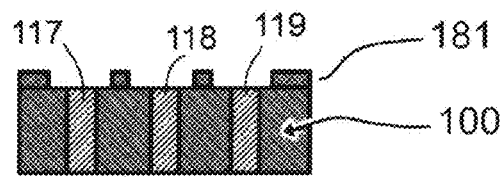
Figure 10A:
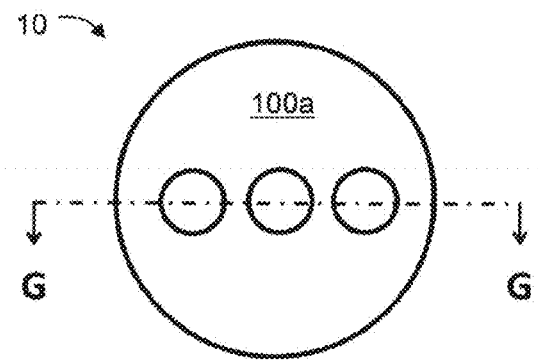
FIGS. 10A-B are schematic illustrations of electrode metal deposited through the masks to form electrodes.
Figure 10B:
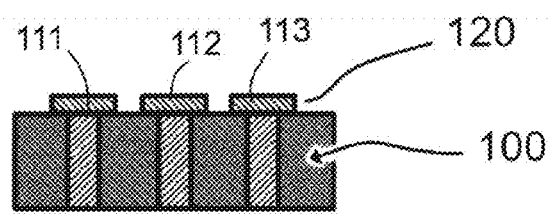

FIGS. 9A-B are schematic illustrations of a stage in the fabrication process in which shadow masks 181 are formed at the front side 100*a* after the vias 117, 118 and 119 are filled with conductive material. The metal can be deposited through shadow masks 181. FIGS. 10A-B are schematic illustrations of a stage in the fabrication process after the metal deposition, wherein the electrode metal is deposited through the masks to form electrodes 111, 112 and 113.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

PDMS Substrate with cPDMS Interconnects

Figure 17A:
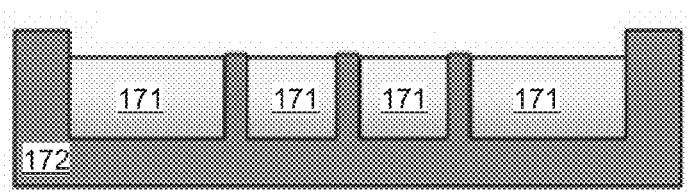
FIGS. 17A-G are schematic illustrations of showing a process employed for fabricating a sensor system during experiments performed according to some embodiments of the present invention.
Figure 17B:
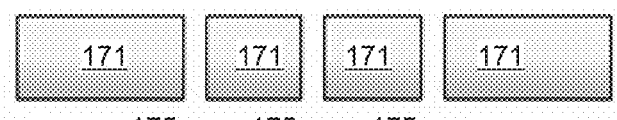
Figure 17C:
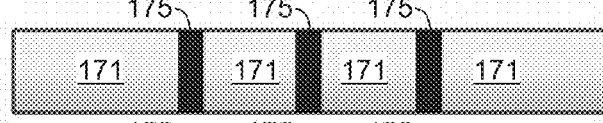
Figure 17D:
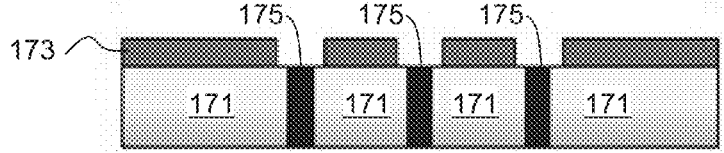
Figure 17E:
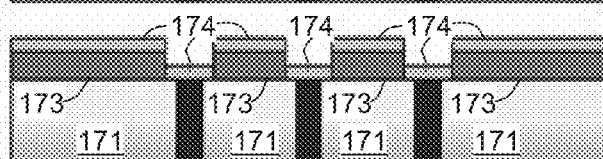
Figure 17F:
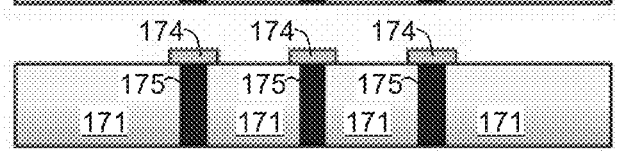
Figure 17G:
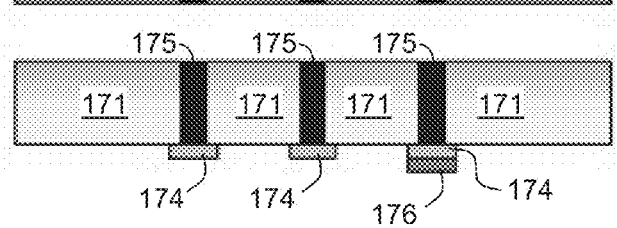

The process employed for fabricating the sensor system is illustrated in FIGS. 17A-G. FIG. 17A illustrates PDMS (171) curing on a 3D printed mold (172) with vias, FIG. 17B illustrates the cured PDMS (171), FIG. 17C illustrates fillings patterns with cPDMS (175), FIG. 17D illustrates a shadow mask (173) deposited on the PDMS (171), FIG. 17E illustrates Gold (174) sputtering, FIG. 17F illustrates mask pilling, and FIG. 17G illustrates fabrication of the reference electrodes.

Mold Fabrication

Initial negative molds were fabricated using a three-dimensional printing process (Objet Connex500™ 3D printing system) from a rigid white polymer (VeroWhitePlus™, in the present example). The molds were then cleaned in a 2% NaOH Solution for at least 30 minutes.

Preparation of PDMS Substrates

PDMS (10:1 v/v mixture of Sylgard 184 and its curing agent) was poured into the mold after degassing (FIG. 17A). The sample was then heated to 55° C. for two hours for curing. PDMS chips were peeled off from the negative mold (FIG. 17B).

Preparation of Conductive PDMS (cPDMS)

PDMS (10:1) was mixed with graphite powder to obtain graphite concentration of ~60 wt %. The substrate trenches and patterns were filled with the cPDMS mixture and curing was at 80° C. for at least 8 hours (FIG. 17C).

Mask Design

A stencil or shadow mask defining the electrodes was drawn using 2D CAD software. The masks were fabricated from polyimide film of 25-75 micron thicknesses (FIG. 17D). Alternatively, metal, plastic, glass, etc. masks may be used.

Electrode/Contact Metallization

Sputter Deposition

The PDMS substrate was placed on a handle wafer with the electrode side facing up. A stencil or shadow mask was placed on the PDMS substrate. An oxygen plasma (5 SCCM, 150 W) was performed for 30 seconds. The substrate was loaded into an ion beam sputterer and 100-300 nm of gold was sputtered onto the exposed cPDMS electrodes (FIG. 17E, FIG. 17F).

Electroplating

In a different experiment, a three-electrode cell containing working electrode (WE), counter electrode (CE) and reference electrode (RE) was fabricated by an electroplating process. The PDMS substrate with cPDMS filled vias was placed in a gold plating bath containing $KAu(CN)_2$-10 g/l of Au. Electrical contact was made with the contact side of the vias and gold was electroplated on the electrode side of the vias.

Reference Electrode Preparation

After sputtering, or electroplating, the formation of reference electrode Ag/AgCl was prepared by a double step process including silver plating of the gold substrate and chloridation of the plated silver (FIG. 17G). The plating was performed and successfully coated the reference electrode (surface area 4 mm$^2$) Immediately after plating of Ag, the Ag electrode was subjected to anodization in HCl for the generation of AgCl salt layer and completion of an Ag/AgCl open reference electrode.

Chip Holder Fabrication

Figures 18A, 18B, 18C, 18D:
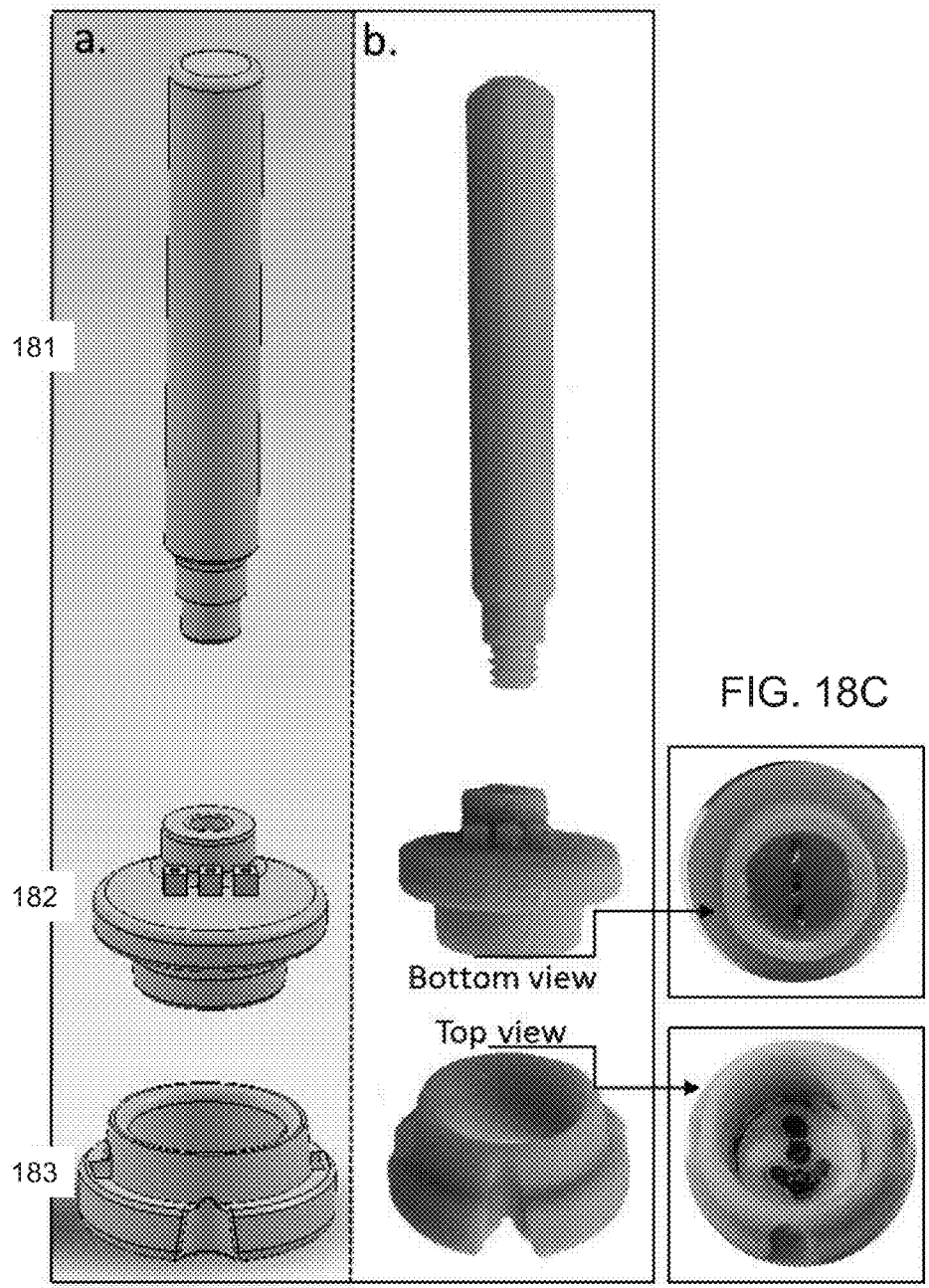
FIGS. 18A-D are schematic illustrations (FIG. 18A) and images (FIGS. 18B-D) of a chip holder fabricated during experiments performed according to some embodiments of the present invention.

A special chip holder for the electrochemical measurements was designed and fabricated using UP Plus™ 3D printer (up3dusa). The chip holder was made from the thermoplastic polymer acrylonitrile butadiene styrene (ABS). The design of a special chip holder for the electrochemical measurements is illustrated in FIG. 18A, and the fabricated holder is shown in FIGS. 18B-D. The chip holder was composed of three parts: hollow handle 181 allowing for device manipulation and wire routing, a cover element 182 containing connectors, and a base element 183 for holding the sensing assembly of the present embodiments. Base element 183 was fabricated with a ring so as to ensure proper sealing against liquid ingress. FIGS. 18A and 18B are exploded views of the holder, FIG. 18C is a bottom view image of cover 182 and FIG. 18D is top view image of base 183.

Example 2

Silicon Substrate with Vias Filled by Electroplating

Via Fabrication

Gold is deposited on one side of a silicon wafer. The other side of the silicon wafer is patterned with lithographic techniques to define the via interconnects. The vias are etched with wet chemical, dry chemical or physical etching until the deposited gold layer is reached. The wafer is placed in an electroplating bath and the vias are filled by electroplating. Chemical mechanical polishing (CMP) is used to create a smooth, uniform surface.

Electrode Patterning

The deposited gold layer is lithographically patterned and etched to define the electrodes.

Reference Electrode Preparation

After the electrodes are patterned the reference electrode Ag/AgCl is prepared by a two-step process of electroplating silver on the reference electrode followed by the chloridation of the plated silver—i.e. the Ag electrode is subjected to anodization in HCl generating an AgCl salt layer thereby completing the Ag/AgCl open reference electrode.

Example 3

Characterization of the Sensor System

A polymer based sensor system was fabricated in accordance with the embodiments of the present invention described in Example 1 above. The electrochemical behavior of the sensor system was evaluated using cyclic voltammetry analysis in the presence of a redox couple of ferrocyanide/ferricyanide electroactive solution.

The parameters were set as follows: the initial potential was set to E=0V, the first switching potential was set to E=0.6V and the second switching potential set to E=−0.3V. The potential step was set to E=0.005V and scan rates between 25 and 150 mVs$^{-1}$ in 1M $KNO_3$. Measurements were performed with a PalmSens® portable potentiostat (Palm Instruments BV, the Netherlands).

Figure 12:
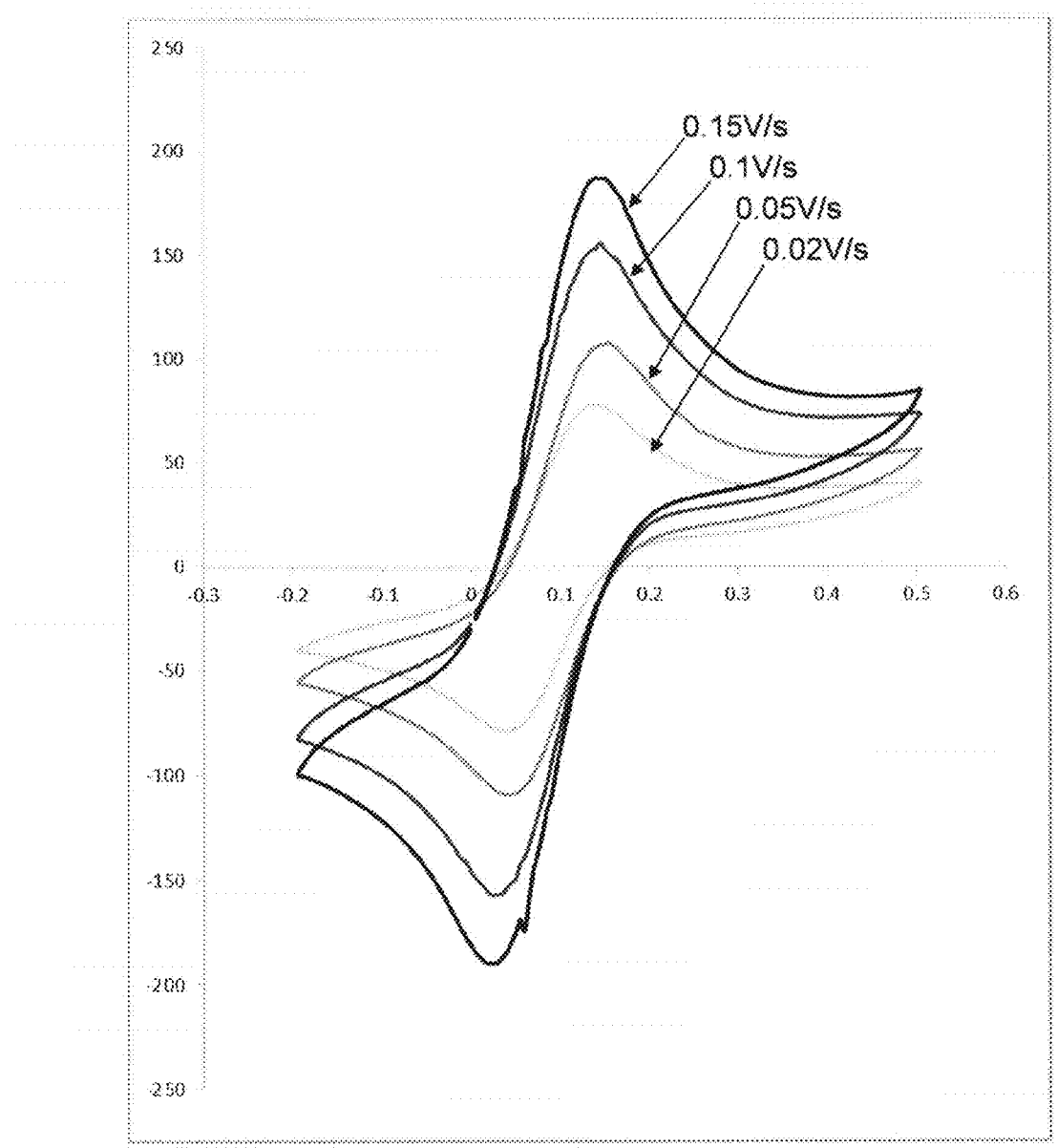
FIG. 12 exemplifies Cyclic voltammogram in 10 mM ferricyanide/ferrocyanide, 1M KNO3 at different scans.

FIG. 12 exemplifies Cyclic voltammogram in 10 mM ferricyanide/ferrocyanide, 1M KNO3 for different scans.

Amperometric detection of the substrate 1-NP was carried out by applying a fixed potential of 0.3 V under a stirred solution. Upon reaching stabilization of the background signal a final concentration of 0.1 mg/ml 1-NP was added. In addition, the determination of ALP activity was carried out by adding the final concentrations of ALP: 10, 1 and 0.5 µg/ml to the chamber.

Figure 13:
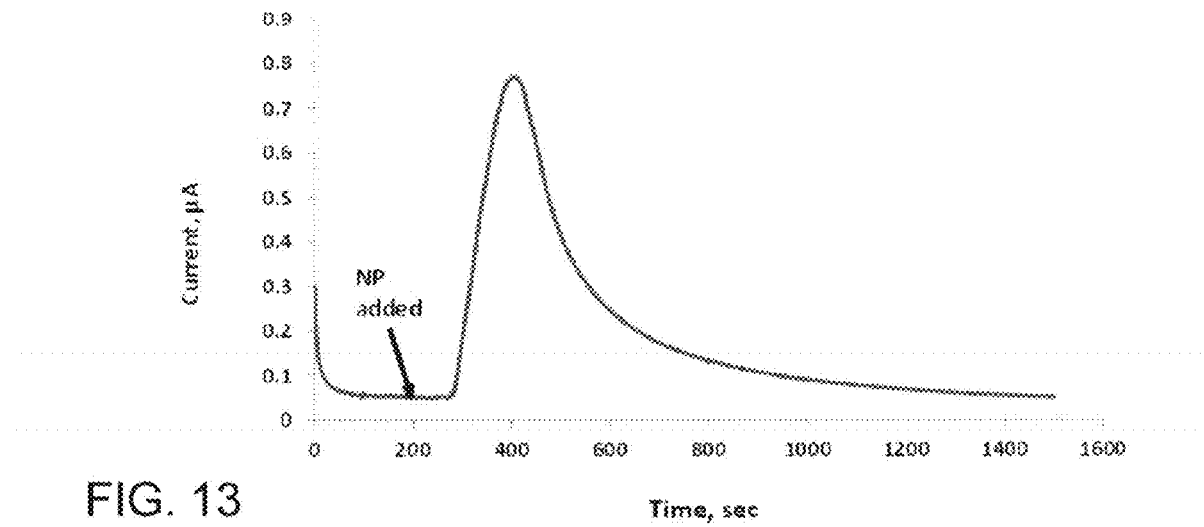
FIG. 13 shows amperometric response to addition of 1-NP in the presence of ALP, at 300 mV as a function of Ag/AgCl.
Figure 14:
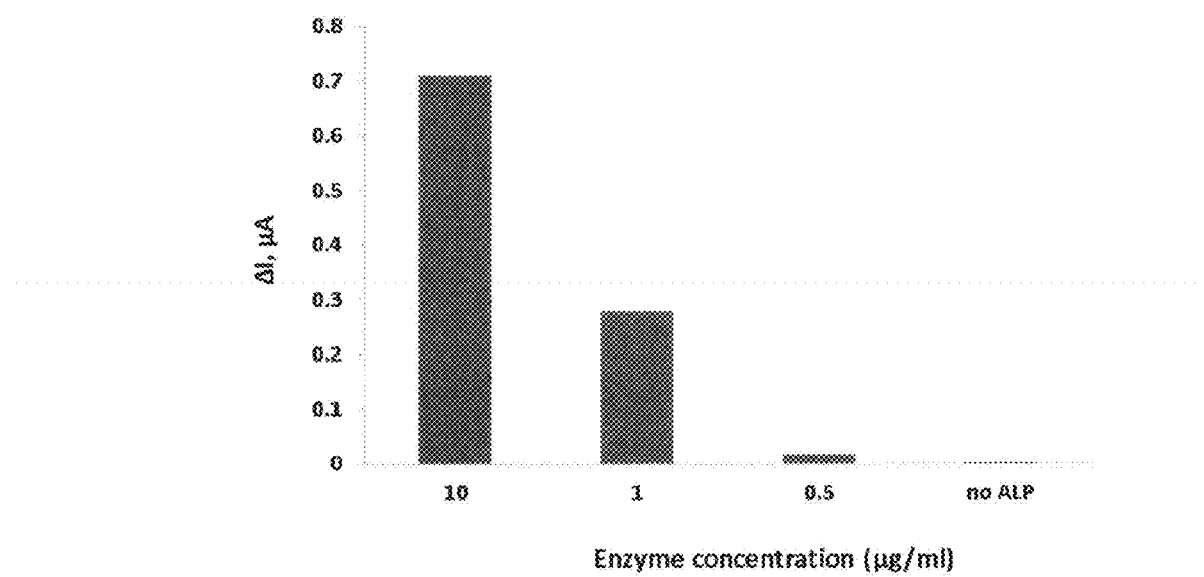
FIG. 14 shows amperometric detection of different ALP concentrations at 300 mV and substrate (1-NP) concentration of 0.1 mg/ml.

FIG. 13 shows amperometric response to addition of 1-NP in the presence of ALP, at 300 mV as a function of Ag/AgCl, and FIG. 14 shows amperometric detection of different ALP concentrations at 300 mV and substrate (1-NP) concentration of 0.1 mg/ml.

The sensor of the present embodiments provides electrochemical signals with high signal-to-noise ratio. High level of adhesion between the gold and the cPDMS was observed. The mechanical properties of cPDMS match those of the PDMS substrate and bending or flexing did not change properties or cause cPDMS to delaminate or crack. The electrode was stable for at least three weeks in storage.

Example 4

Electrical Sensing

A polymer based sensor system having a flexible substrate and Au/AgPDMS electrodes was fabricated in accordance with the embodiments of the present invention described in Example 1 above.

Electrocardiogram (ECG) Signal

The sensor system was placed on the surface of the skin of a volunteer in the presence of electrolyte gel, and ECG signal was recorded by an external device. For comparison, commercial ECG stickers (SKINTACT ECG Electrode F-RG1/6) were also attached to the skin of the same volunteer.

Figures 15A, 15B:
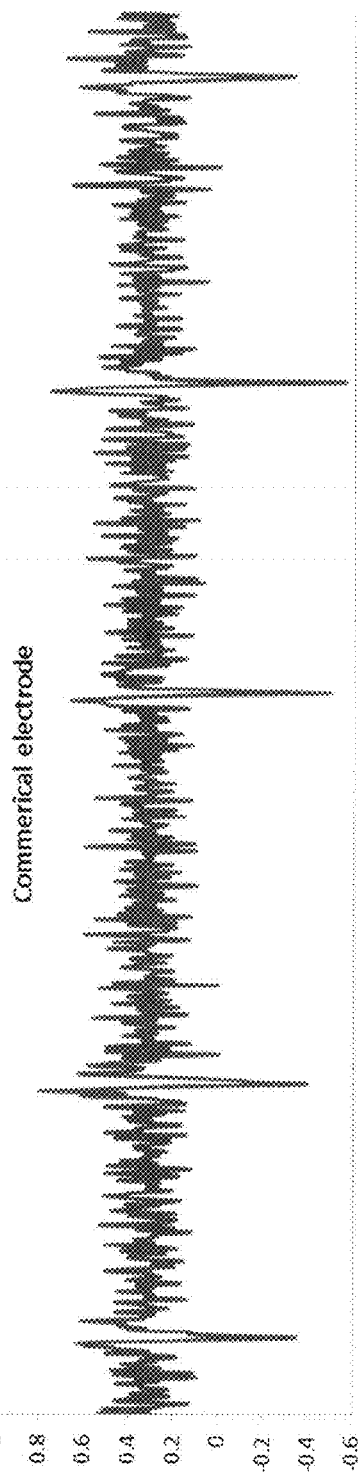
FIGS. 15A-B show an ECG signal as sensed by commercial stickers (FIG. 15A), and by a sensor system prepared according to some embodiments of the present invention (FIG. 15B)

FIG. 15A shows an ECG signal as sensed by the commercial stickers, and FIG. 15B shows an ECG signal as sensed by the sensor system of the present embodiments. As shown the signal quality and signal-to-noise-ratio (SNR) were higher for the sensor system optionally and preferably than for the commercial sticker.

Local Field Potential Measurement

A local field potential (LFP) is a particular class of electrophysiological signals, which is dominated by the electrical current flowing from all nearby dendritic synaptic activity within a volume of tissue.

The sensor system of the present embodiments was used for sensing LFP signal from a rat brain. For comparison, a commercial LFP sensor (5 MOhm at 1 kHz tungsten electrode by A-M Systems) was also used to record LFP signal from the same rat.

Figure 16A:
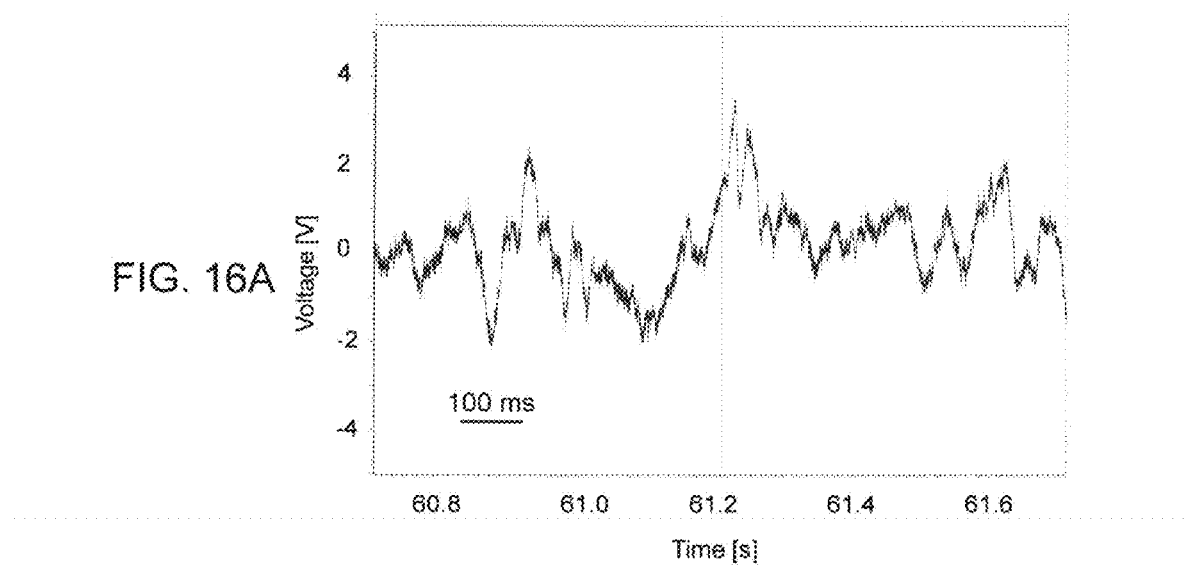
FIGS. 16A-F show results of experiments in which local field potential signals were sensed according to some embodiments of the present invention.
Figure 16B:
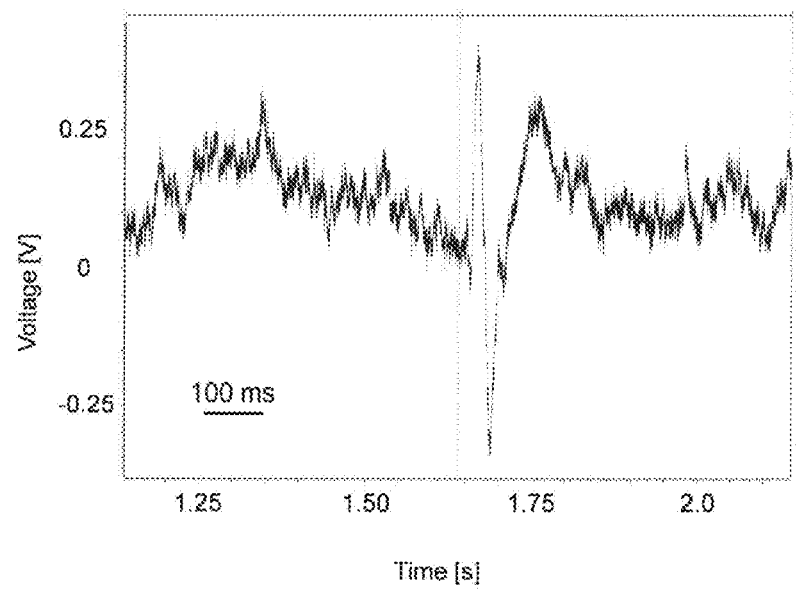
Figure 16C:
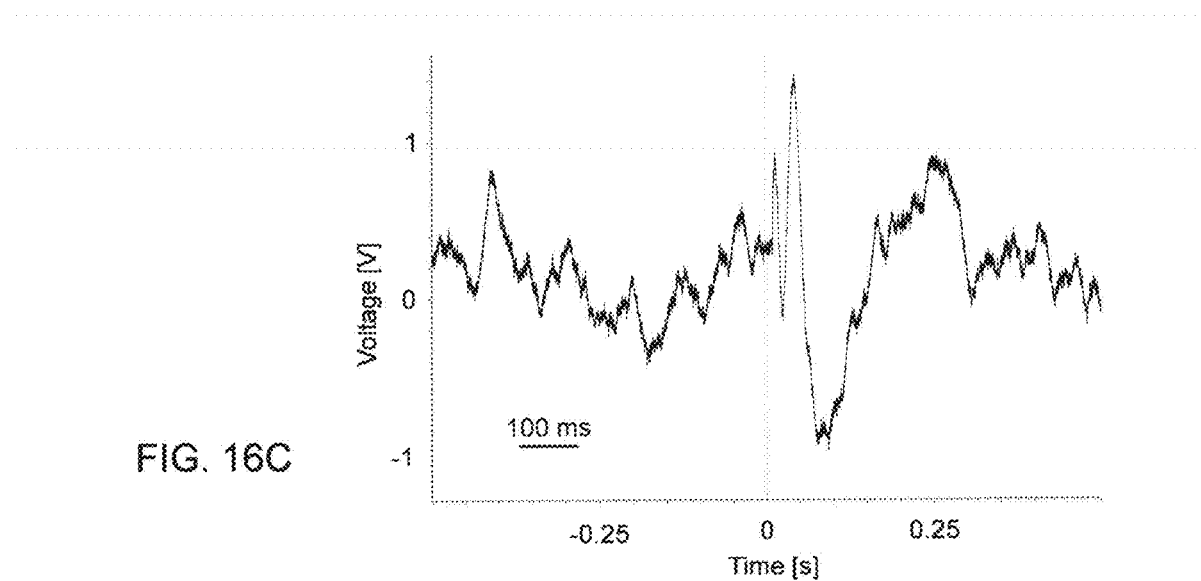
Figure 16D:
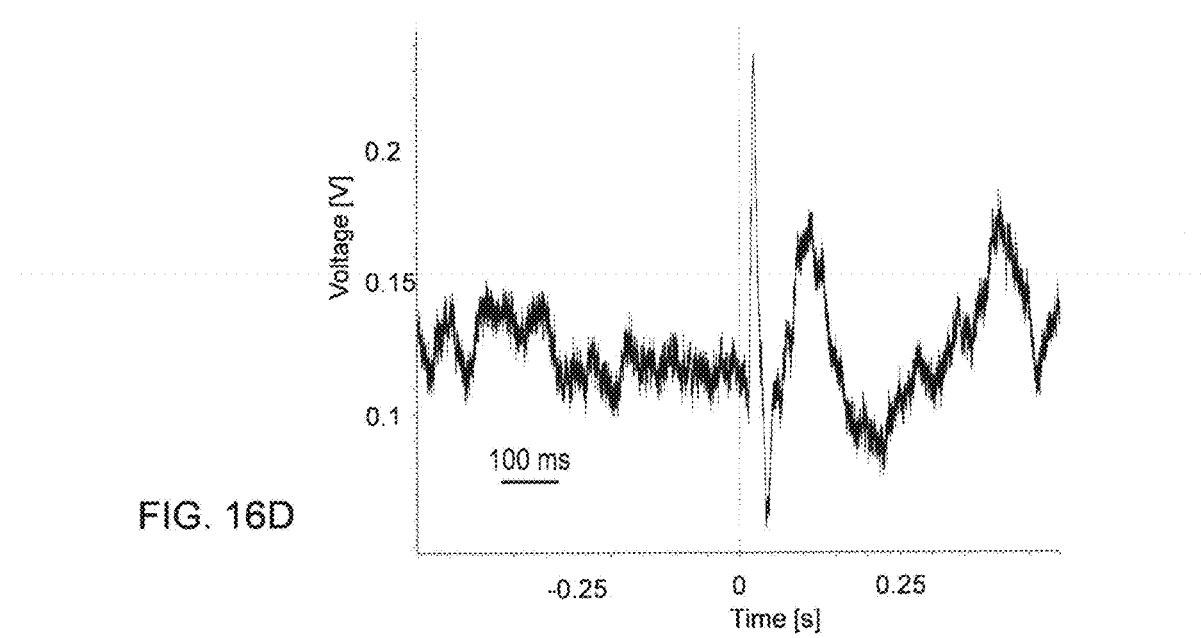
Figure 16E:
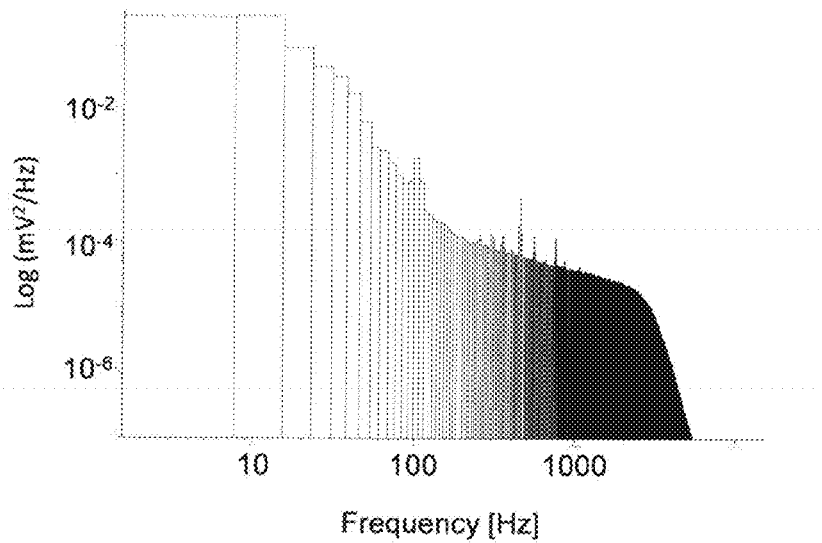
Figure 16F:
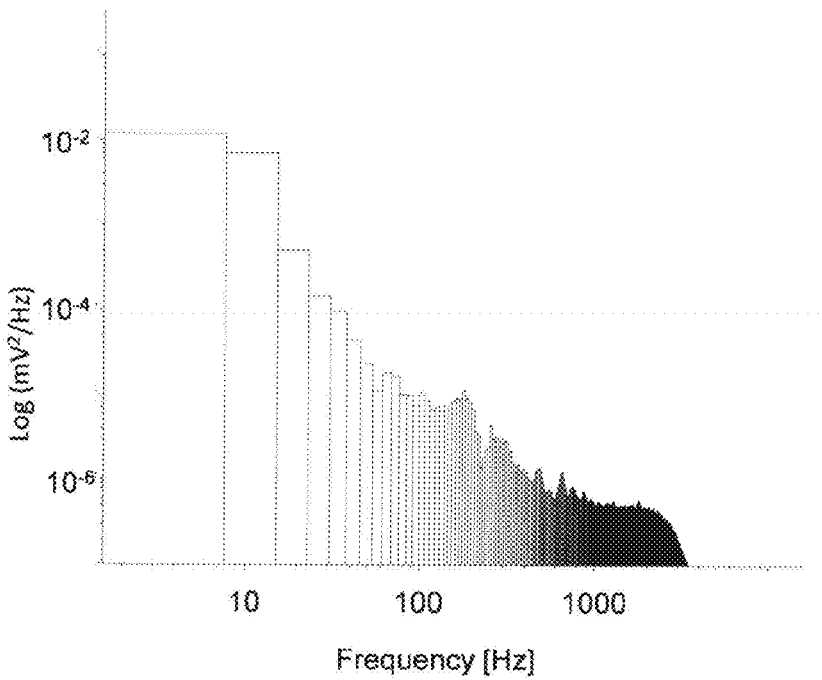

The results are shown in FIGS. 16A-F for LFP signals sensed by the commercial sensors (FIGS. 16A, 16C and 16E) and the sensor system of the present embodiments (FIGS. 16B, 16D and 16F), where FIGS. 16A and 16B show example trials, FIGS. 16C and 16D show average waveforms, and FIGS. 16E and 16F show power spectra.

Electrochemical Measurements in a Multi-Well Cell Culture Plate

Three types of colon cancer cell lines were studied: HT29, HCT116 and Colo320. Cells were grown in Dulbecco's Minimal Essential Medium containing fetal bovine serum 10%, glutamine 1% (2 mM) and antibiotics 1% (100 units/mL penicillin, 100 µg/mL streptomycin, 1250 units/mL nystatin), at 37° C. in a 5% $CO_2$ atmosphere.

For a feasibility demonstration of direct in-vitro cells monitoring by the sensor system of the present embodiments, the electrochemical response to secreted ALP enzyme levels was investigated. Most human tissues contain ALP: kidney, liver, bone, intestine and placenta are rich sources. ALP is a secreted enzyme from cells and is used as a marker to distinguish between normal and cancer cells. Changes in ALP levels are highly important in the clinical area. The ALP activity was measured after the addition of the substrate p-aminophenyl phosphate (pAPP) to the cell culture. pAPP undergoes dephosphorilation by the enzyme yielding the product p-aminophenol (pAP) which is subsequently oxidized to iminoquinone on the working electrode at low positive potential of 220 mV vs Ag/AgCl and chronoamperometrically monitored for 1 hour. The electrochemical reaction is described in Diagram 1, below.

Diagram 1

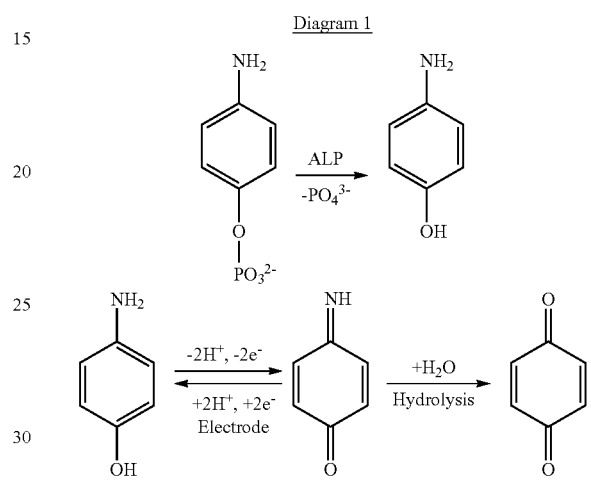

Figure 19A:
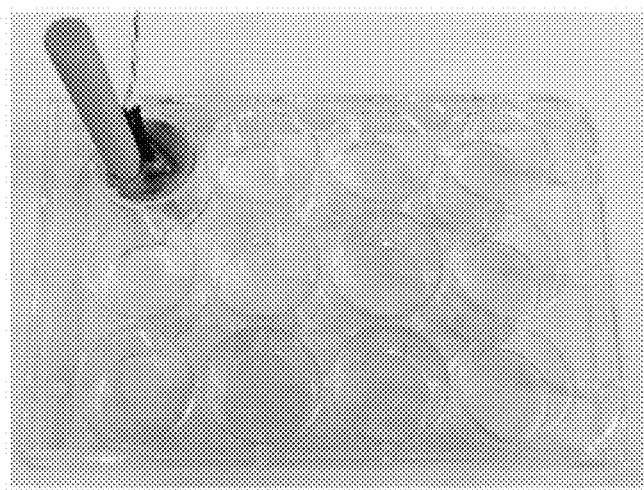
FIGS. 19A-C are an experimental setup image (FIG. 19A) and experimental results (FIGS. 19B-C) of an experiment in which electrochemical measurements were performed directly in a multi-well cell culture plate, according to some embodiments of the present invention.

The electrochemical measurements performed directly in a 12-well cell culture plates. The sensor system of the present embodiments was mounted on the holder described above and was placed inside the well, as shown in FIG. 19A. Upon reaching confluence cells were washed and re-suspended in PBS solution (pH 7.2). The pAPP substrate was added (a final concentration of 0.1 mg/mL) following a short equilibration time, allowing for the stabilization of the system and determination of the background signal emerging from background electrochemical and biochemical reactions. In addition, calibration experiments of different ALP concentrations (in the range of 250 ng/ml-10 µg/ml) as free enzyme in solution were conducted. All measurements were performed using a PalmSens portable potentiostat (Palm Instruments BV, the Netherlands) at room temperature.

Figure 19B:
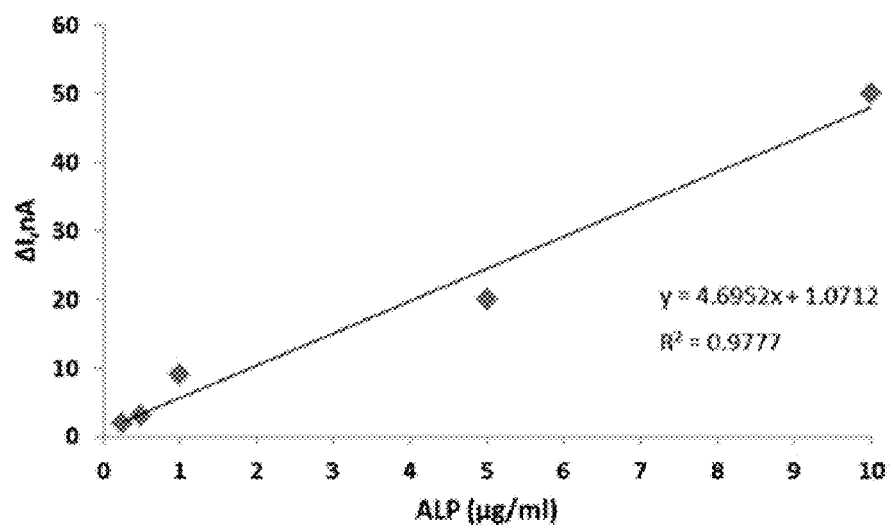
Figure 19C:
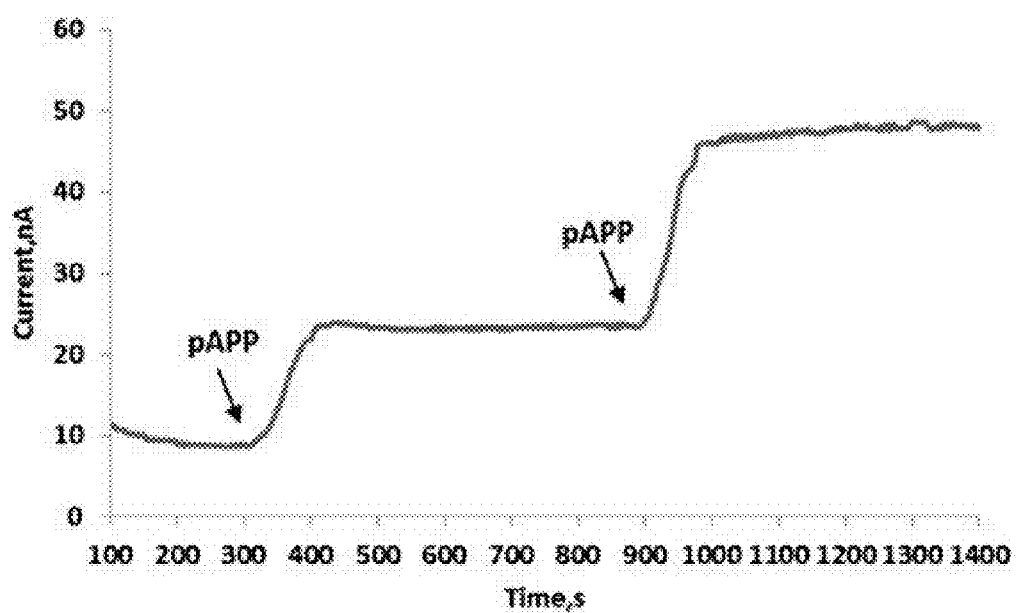

Results of the experiment are exemplified in FIGS. 19B and 19C, where FIG. 19B shows a calibration curve of different ALP concentrations at 220 mV with substrate (pAPP) concentration of 0.1 mg/ml, and FIG. 19C shows a representative current response of Colo320 cells to the addition of pAPP (0.1 mg/ml) at 300 s and 900 s. ALP concentrations levels secreted from the cell lines are listed in Table, below.

TABLE 1

| | ALP concentration [µg/ml] |
| --- | --- |
| Colo320 | 3.027 ± 2.93 |
| HCT116 | 1.774 ± 1.97 |
| HT29 | 1.390 ± 0.89 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A sensor system, comprising:
   a flexible substrate, having a front side and a back side;
   a sensing assembly having a plurality of electrodes formed on said front side and being configured to provide electrochemical sensing;
   a plurality of electrical contacts, formed on said back side and being in electrical communication with said sensing assembly via a plurality of interconnects passing through said substrate and extending at least from said front side to said back side; and
   a mounting member configured for mounting said back side onto a tip of a movable device;
   wherein when said flexible substrate is contacted with a target substance, said flexible substrate containing said electrodes deform, causing said electrodes to conform with a shape of said target substance and to contact said target substance.

2. The system according to claim 1, wherein said movable device is a hand-held device.

3. The system according to claim 1, wherein said movable device is a movable arm of a robot.

4. The system according to claim 1, wherein said movable device is an internal medical tool selected from the group consisting of an endoscope, a laparoscope and a cannula, and wherein said substrate is adapted for being introduced into the body of a mammal via endoscopic procedure.

5. The system according to claim 1, wherein said movable device is an external medical tool.

6. The system according to claim 1, wherein said substrate is sizewise comparable with said tip.

7. The system according to claim 6, wherein said electrochemical sensing assembly comprises at least a working electrode, a reference electrode and a counter electrode.

8. The system according to claim 1, wherein said front side is non-adhesive to tissue.

9. The system according to claim 1, wherein said electrochemical sensing assembly comprises at least a working electrode, a reference electrode and a counter electrode.

10. The system according to claim 9, wherein said interconnects have a shape selected from the group consisting of a generally conical shape, a generally cylindrical shape, and an hourglass shape.

11. The system according to claim 1, wherein said interconnects have a shape selected from the group consisting of a generally conical shape, a generally cylindrical shape, and an hourglass shape.

12. The system according to claim 1, further comprising said movable device.

13. The system according to claim 1, wherein said mounting member comprises an adhesive.

14. The system according to claim 1, wherein said mounting member comprises a housing configured to receive said substrate at a front side of said housing and said movable device at a back side of said housing.

15. A method, comprising providing a movable device and mounting the sensor system according to claim 1, on said movable device using said mounting member.

16. A method of sensing a target substance, comprising contacting the target substance with the system according to claim 1, and receiving signals from said plurality of electrical contacts, thereby sensing the target substance.

17. The system according to claim 1, comprising a plurality of electrical leads connectable to a measuring device, and a lever configured for pushing said leads to engage said electrical contacts.

* * * * *